(12) United States Patent
Fisher et al.

(10) Patent No.: US 6,994,712 B1
(45) Date of Patent: Feb. 7, 2006

(54) BIOABSORBABLE MARKER HAVING EXTERNAL ANCHORING MEANS

(75) Inventors: John S. Fisher, Belleair, FL (US); Frederick Ahari, Tucson, AZ (US)

(73) Assignee: Biopsy Sciences, LLC, Clearwater, FL (US)

( * ) Notice: Subject to any disclaimer, the term of this patent is extended or adjusted under 35 U.S.C. 154(b) by 463 days.

(21) Appl. No.: 10/065,704

(22) Filed: Nov. 12, 2002

(51) Int. Cl.
 *A61B 19/00* (2006.01)
(52) U.S. Cl. ............... 606/116; 600/434; 600/365; 128/899; 604/164; 604/264
(58) Field of Classification Search ........ 600/407–482, 600/365; 128/899; 606/116; 604/164, 264
See application file for complete search history.

(56) References Cited

U.S. PATENT DOCUMENTS

| 5,749,922 | A | | 5/1998 | Slepian et al. |
| 5,782,771 | A | * | 7/1998 | Hussman .................... 600/478 |
| 5,865,738 | A | * | 2/1999 | Morcos et al. ............... 600/365 |
| 6,228,055 | B1 | * | 5/2001 | Foerster et al. ............. 604/116 |
| 6,356,782 | B1 | * | 3/2002 | Sirimanne et al. .......... 600/431 |
| 6,405,733 | B1 | * | 6/2002 | Fogarty et al. ............. 128/899 |
| 2001/0046518 | A1 | | 11/2001 | Sawhney |

\* cited by examiner

*Primary Examiner*—Ali Imam
*Assistant Examiner*—William C. Jung
(74) *Attorney, Agent, or Firm*—Ronald E. Smith; Smith & Hopen, P.A.

(57) ABSTRACT

A clip and a bioabsorbable marker are employed to mark a biopsy site. The former provides a permanent marker that is clamped onto tissue and that cannot migrate from the site over time. The latter is gradually bioabsorbed over time but the time may vary widely from weeks to months. In most embodiments, the clip and marker are integrally formed with one another at the time of manufacture. In one embodiment, the clip and marker are independently made but are joined to one another during the site-marking process. The markers are deployed by core biopsy needles of the type employing a vacuum, of the type that does not employ a vacuum, and by coaxial biopsy needles.

46 Claims, 26 Drawing Sheets

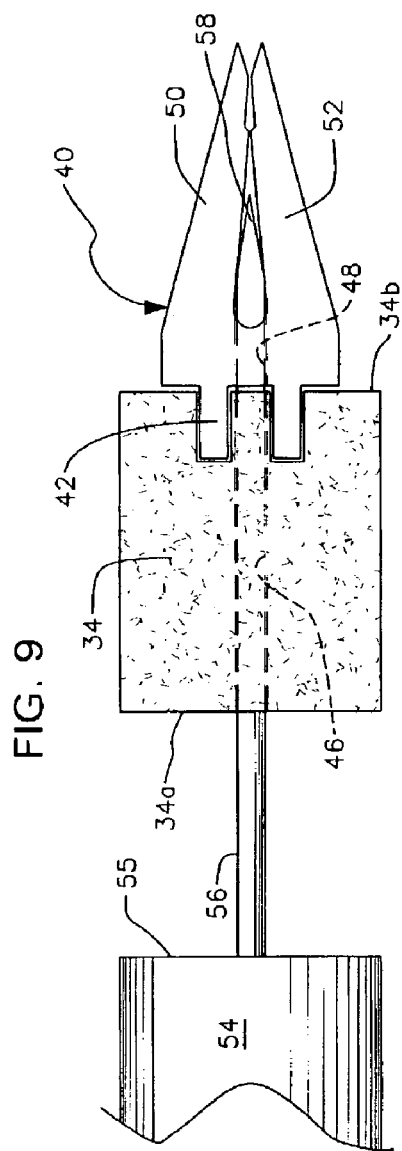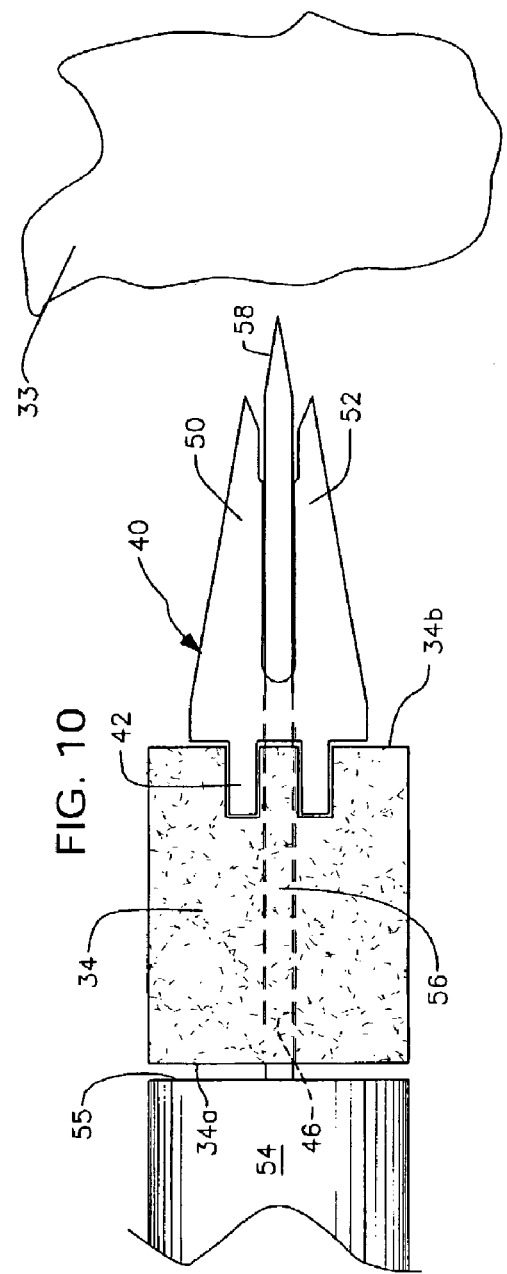

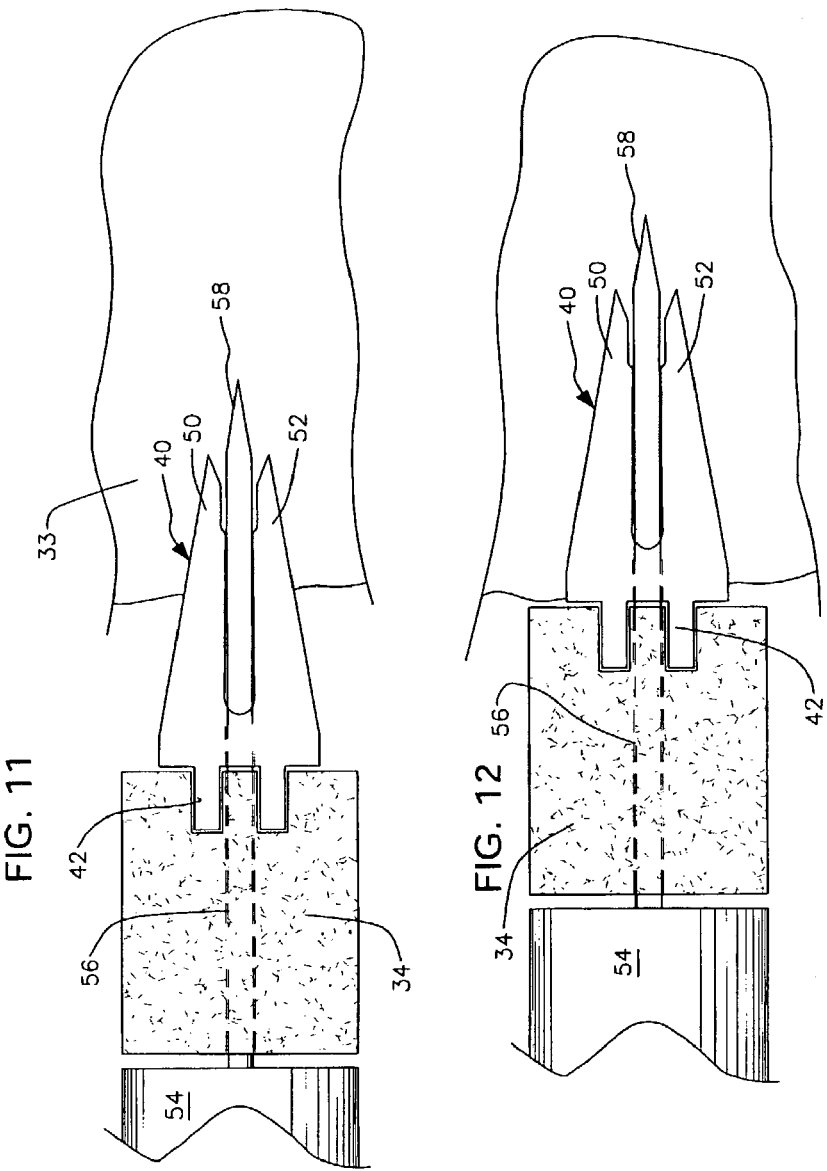

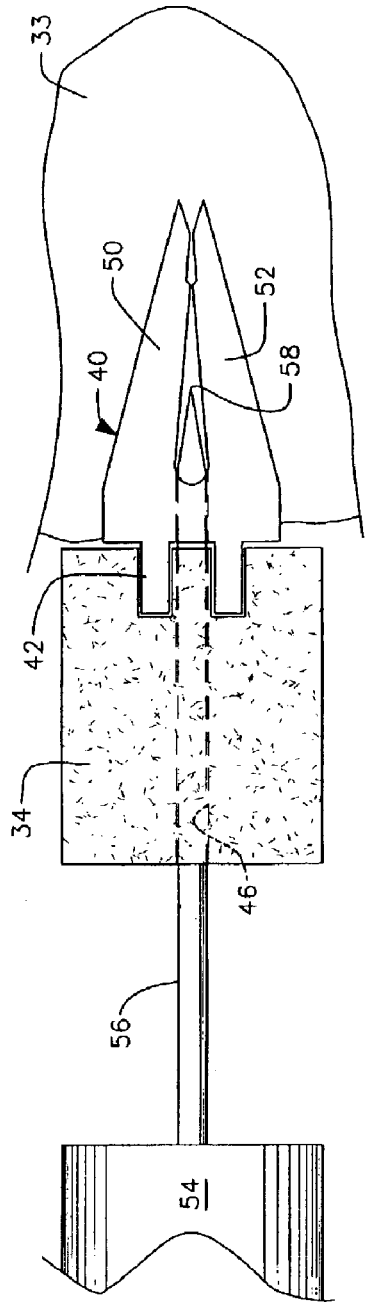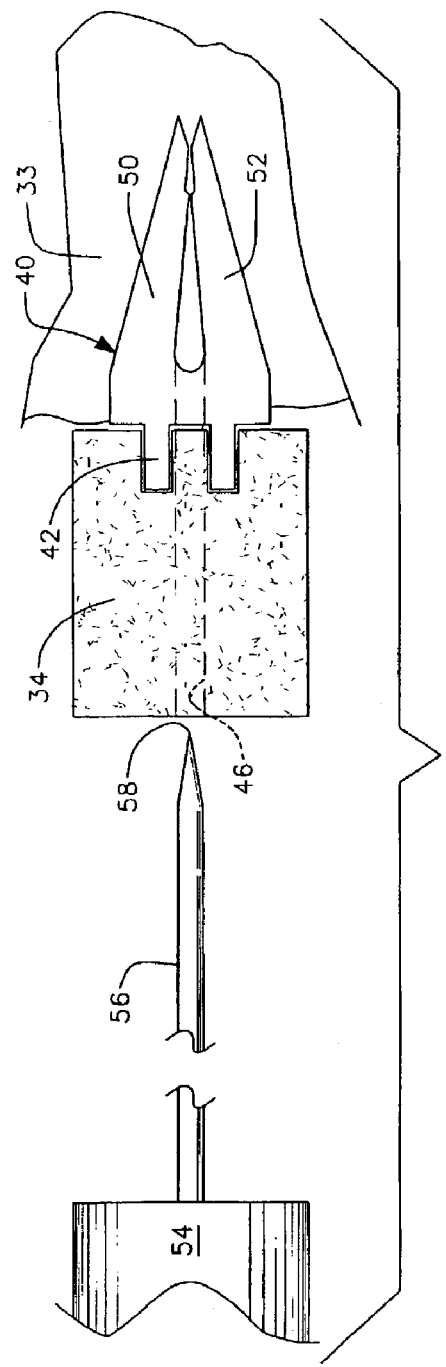
FIG. 13
FIG. 14

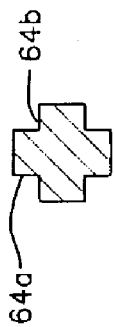
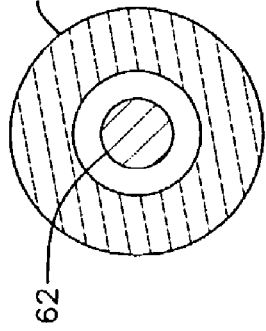
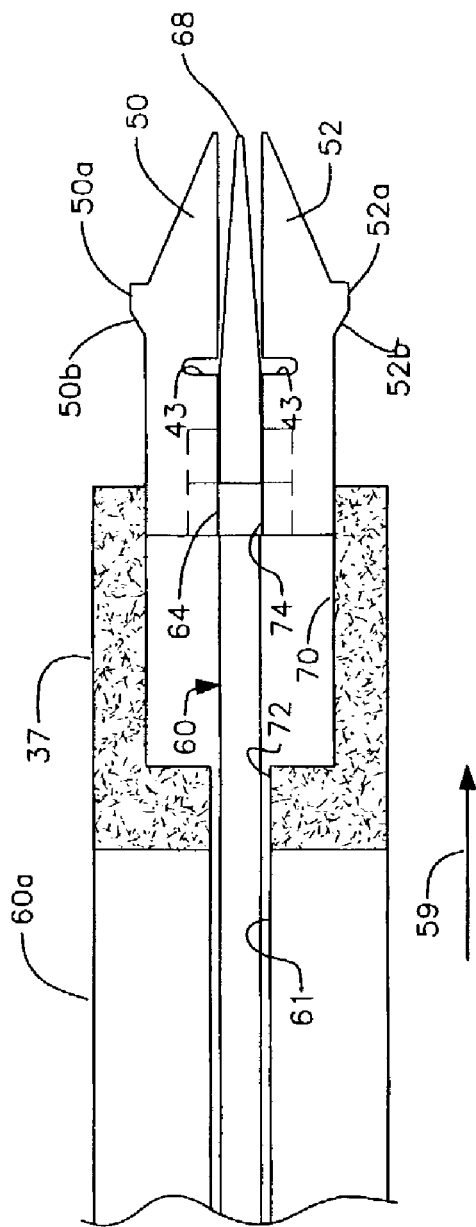

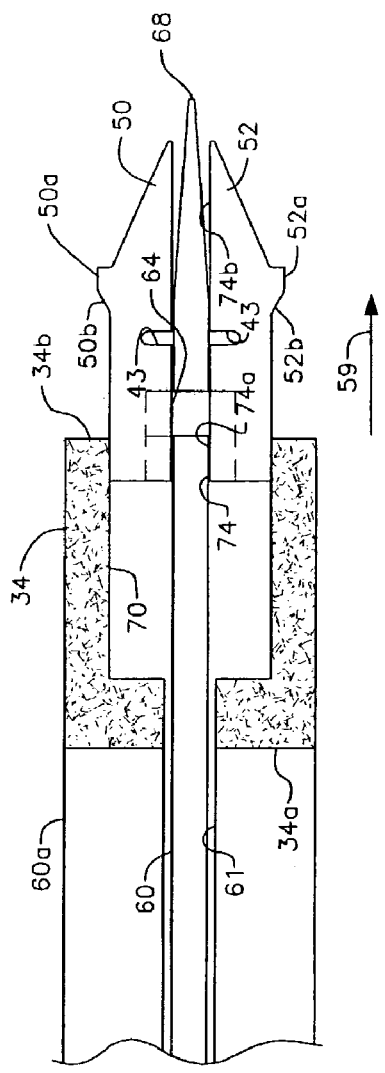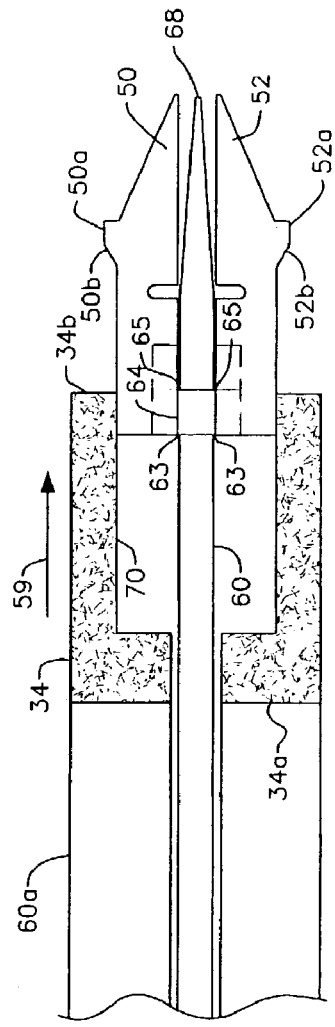

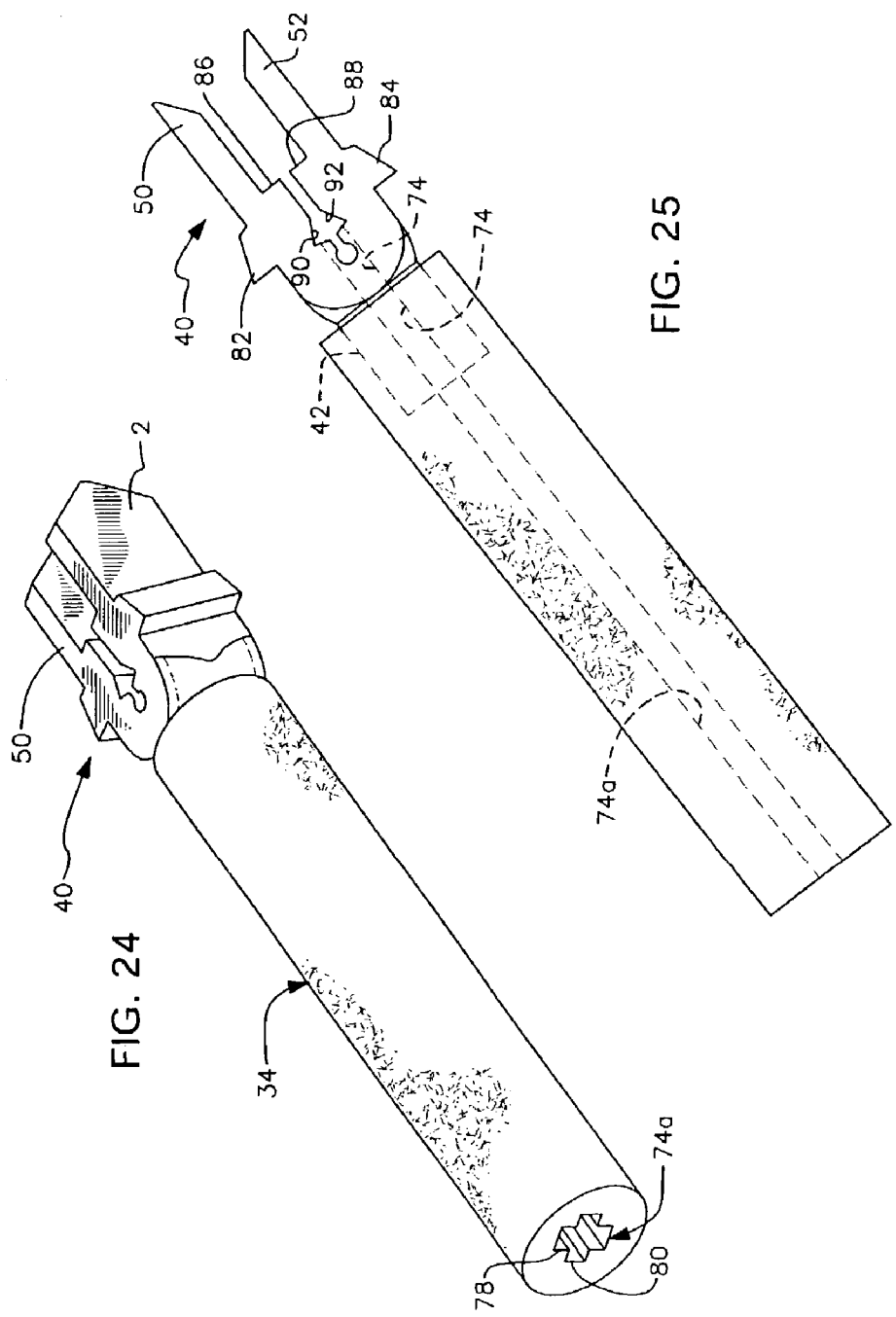

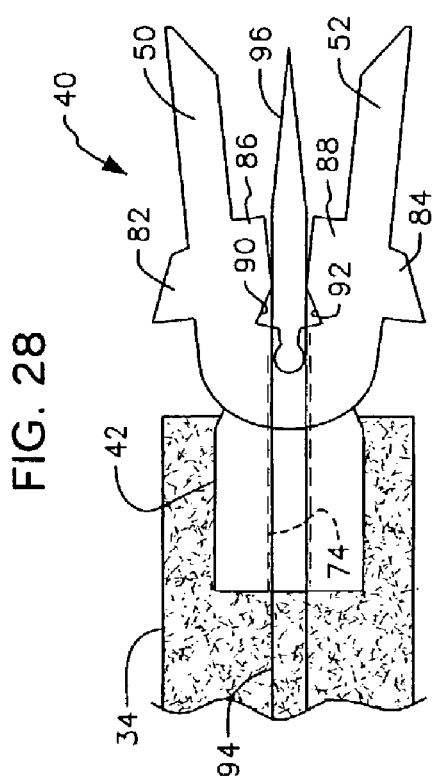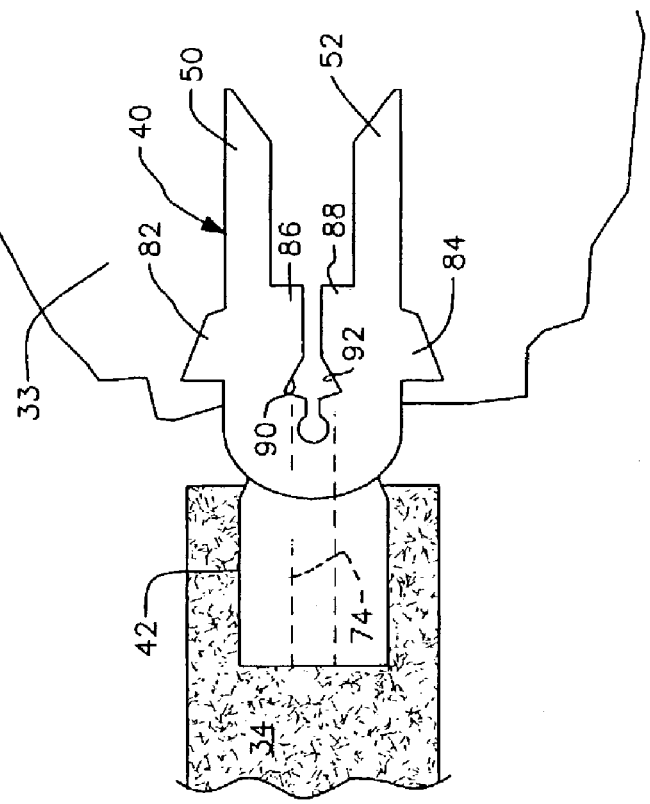

BIOABSORBABLE MARKER HAVING EXTERNAL ANCHORING MEANS

BACKGROUND OF INVENTION

1. Field of the Invention

This invention relates, generally, to tissue markers. More particularly, it relates to a bioabsorbable marker having an anchoring means that is not bioabsorbable and that is external to the bioabsorbable part of the marker.

2. Description of the Prior Art

Placing a marker in or near a lesion or tumor upon which a biopsy procedure has been performed enables a physician to find the lesion or tumor at a date weeks or months after the biopsy, depending upon the rate of degradation of the marker. The marker may be observed under ultrasound, it may be radiopaque, or the like.

In some cases, the marker material may be completely bioabsorbed by the time the physician needs to locate the lesion or tumor again. One of the ways to enable such re-finding of the lesion or tumor is to attach a metallic marker to the bioabsorbable marker so that the metallic marker may be found by X-ray or other techniques long after the marker has been bioabsorbed.

However, metallic markers are prone to migrate within the tissue. Thus, when they are found after the passage of an extent of time, they may have migrated from their initial position in or near the lesion or tumor, thereby destroying their functionality as a marker to accurately mark the biopsy site.

What is needed, then, is a bioabsorbable marker having a metallic part that does not migrate after the bioabsorbable material of the marker has been absorbed by a patient's body.

However, in view of the prior art considered as a whole at the time the present invention was made, it was not obvious to those of ordinary skill in the pertinent art how the identified need could be fulfilled.

SUMMARY OF INVENTION

The long-standing but heretofore unfulfilled need for a bioabsorbable marker having a metallic part that does not migrate after the bioabsorbable material of the marker has been absorbed by a patient's body is now met by a new, useful, and nonobvious invention.

In a first embodiment of the novel tissue marker means, a biologically absorbable marker has a trailing end and a leading end. A metal wire of straight configuration has a trailing end embedded within the leading end of the biologically absorbable marker and a leading end of the metal wire is disposed in leading relation to the leading end of the biologically absorbable marker.

A delivery catheter has an anvil means fixedly secured within a lumen of the delivery catheter at a leading end of the delivery catheter. The anvil has a cavity formed therein that causes bending of the straight wire into a hook shape when the straight wire is driven in a trailing-to-leading direction into the cavity.

Without restriction to the particular apparatus of the first embodiment, the method of the first embodiment includes the steps of fixedly securing a trailing end of a straight wire into a leading end of a tissue marker means, providing a delivery catheter having a side port and means for communicating a vacuum to a lumen of the delivery catheter, fixedly securing an anvil means within the lumen of the delivery catheter at a leading end of the delivery catheter in leading relation to the side port, forming a blind bore having a concave bottom in the anvil, introducing the tissue marker means into the lumen of the delivery catheter from a trailing end of the delivery catheter, introducing the delivery catheter into a biopsy needle having a side port so that the respective side ports of the delivery catheter and biopsy needle are in substantial registration with one another, applying a vacuum to the biopsy needle so that tissue is pulled into the lumen of the delivery catheter, pushing the tissue marker means in a trailing-to-leading direction toward the leading end of the delivery catheter so that the free leading end of the straight wire penetrates tissue that has been pulled under vacuum into the lumen of the delivery catheter and so that the free leading end of the straight wire then enters into the blind bore and is bent into a hook shape when said leading end encounters the concave bottom of the cavity and is constrained to form a return bend as the pushing of the tissue marker means continues, and removing the biopsy needle and delivery catheter from the tissue site so that only the biologically absorbable marker and the wire remain at the site whereby the wire engaging the tissue prevents migration of the biologically absorbable marker and of the wire.

There is no requirement in the first embodiment, or any other embodiment, that the marker be biologically absorbable. Such feature is merely preferable but not critical.

Nor must the means for anchoring the marker against migration necessarily be formed of metal. Instead of metal, an injection-molded plastic member could be employed, as long as the injection-molded member is observable under ultrasound, CT scan, x-ray, MRI, or other imaging technique. Nor is the anchoring means limited to metal or plastic; any material that can be formed into a clip or hook, which can be seen under at least one imaging technique, and which is not toxic to a mammalian body can be employed in lieu of a metallic or plastic clip, hook, or other anchoring means. The anchoring means may be bioabsorbable or non-bioabsorbable. Where a bioabsorbable anchoring means is employed, it should be formed of materials enabling the amount of time required for bioabsorption to be controllable.

In a second embodiment of the novel apparatus for anchoring a tissue marker to a tissue site, the structure includes a tissue marker of generally cylindrical configuration. A first bore is formed in the tissue marker in coincidence with a longitudinal axis of symmetry of the tissue marker. The first bore extends from a trailing end to a leading end of the tissue marker.

An annular cavity is formed in a leading end of the tissue marker in concentric relation to the bore. A clip formed of metal or other suitable material has opposed jaws disposed in a normally closed configuration where respective free ends of the jaws are in close juxtaposition with one another. The clip has an annular base formed in a trailing end thereof. The annular base is received within and fixedly secured to the annular cavity.

A second bore is formed in the clip in coincidence with a longitudinal axis of symmetry thereof. The second bore is in axial alignment with the first bore when the annular base of the clip is received within the annular cavity of the tissue marker.

A plunger has a first part of generally cylindrical configuration. The first part has a diameter substantially equal to a diameter of the tissue marker so that the first part and the tissue marker are adapted to be slideably received within a delivery catheter. The plunger has a reduced diameter second part with a pointed leading end for penetrating tissue.

A second part of the plunger has an elongate extent sufficient to extend sequentially through the first bore formed in the tissue marker, the second bore formed in the clip, and between the opposed jaws. The pointed leading end of the second part is disposed in leading relation to a leading end of the jaws when the plunger is fully introduced into the delivery catheter. Accordingly, the second part causes the opposed jaws to diverge from one another when inserted therebetween. The opposed jaws converge toward one another under their inherent bias when the second part of the plunger is withdrawn.

Without limitation to the particular structure of the second embodiment, a second method for anchoring a tissue marker to a tissue site includes the steps of providing a tissue marker of generally cylindrical configuration, forming a first bore in the tissue marker in coincidence with a longitudinal axis of symmetry thereof so that the first bore extends from a trailing end to a leading end of the tissue marker, forming an annular cavity in a leading end of the tissue marker in concentric relation to the bore, providing a clip having opposed jaws disposed in a normally closed configuration where respective free ends of the jaws are in close juxtaposition with one another, forming an annular base formed in a trailing end of the clip so that the annular base is received within and fixedly secured to the annular cavity, forming a second bore in the clip in coincidence with a longitudinal axis of symmetry of the clip so that the second bore is in axial alignment with the first bore when the annular base of the clip is received within the annular cavity of the tissue marker, providing a plunger having a first part of generally cylindrical configuration, the first part having a diameter substantially equal to a diameter of the tissue marker so that the first part and the tissue marker are adapted to be slideably received within a delivery catheter, providing the plunger with a reduced diameter second part with a pointed leading end for penetrating tissue, forming the second part to have an elongate extent sufficient to extend sequentially through the first bore formed in the tissue marker, the second bore being formed in the clip, and between the opposed jaws so that said pointed leading end of the second part is disposed in leading relation to a leading end of said jaws when the plunger is fully introduced into the delivery catheter so that the second part causes the opposed jaws to diverge from one another when inserted therebetween and so that the opposed jaws converge toward one another under their inherent bias when the second part of the plunger is withdrawn.

A third embodiment of the novel apparatus for anchoring a tissue marker to a tissue site includes a marker of generally cylindrical configuration having a leading end and a trailing end. A first bore is formed in the trailing end of the marker in coincidence with a longitudinal axis of symmetry of the marker. A second bore is formed in the leading end of the marker in coincidence with a longitudinal axis of symmetry thereof. The first and second bores are in open communication with one another. The second bore has a diameter greater than a diameter of said first bore.

A clip has a trailing end and a leading end. The trailing end is adapted to be received within the second bore.

A third bore is formed in the trailing end of the clip in coincidence with a longitudinal axis of symmetry of the clip. The third bore is cross-shaped in transverse cross-section.

An inner plunger has a leading end with a circular transverse cross-section of predetermined extent and a pointed distal end of predetermined extent that is adapted to penetrate tissue. The pointed distal end is formed integrally with the leading end and is positioned in leading relation thereto. The inner plunger has a trailing end with a circular transverse cross-section and a middle part with a cross-shaped transverse cross-section adapted to be slidingly received within the cross-shaped third bore. The middle part is formed integrally with the leading and trailing ends of the plunger and is disposed therebetween.

An outer plunger has a central bore adapted to slidingly receive the trailing end of the inner plunger. The outer plunger also has a leading end adapted to abuttingly engage the trailing end of the marker.

A first radially outwardly extending protuberance is formed on a first jaw of the clip and a second radially outwardly extending protuberance is formed on a second jaw of the clip. The first protuberance has a first beveled trailing surface and the second protuberance has a second beveled trailing surface. The first and second opposed jaws are driven toward one another when the marker is driven in a trailing to leading direction by the outer plunger. The leading end of the marker slideably engages the first and second beveled surfaces and drives the first and second beveled surfaces toward one another.

The middle part of the inner plunger is positioned on a trailing side of the third bore and is rotationally misaligned with the cross-shaped third bore so that a trailing end of the middle part is disposed in abutting relation to a leading end of the third bore to prevent travel of the clip in a trailing-to-leading direction when the inner plunger is held against movement in the trailing-to-leading direction. Accordingly, the inner plunger is held against movement in the trailing-to-leading direction, thereby holding the clip against movement in the trailing-to-leading direction, and the outer plunger is displaced in a trailing-to-leading direction to drive the marker in the trailing-to-leading direction. The leading end of the marker enters into sliding engagement with the first and second beveled surfaces, driving them into converging relation with one another. The respective leading ends of the opposed jaws are driven into the tissue by continued trailing-to-leading displacement of the outer plunger. When the jaws are fully embedded within the tissue, a part of the tissue is captured between the jaws.

The marker when driven in a trailing-to-leading direction slideably receives the trailing end of the clip into the second bore. Longitudinal displacement of the inner plunger in the trailing-to-leading direction and rotation of the inner plunger about its longitudinal axis of symmetry until the middle part aligns with the cross-shaped cross section of the third bore, followed by retraction of the inner plunger in a leading-to-trailing direction until the inner plunger has exited the first bore leaves the clip secured to the tissue and the marker secured to the trailing end of the clip.

A beveled surface is formed in the leading end of the marker to facilitate sliding engagement of the first and second trailing beveled surfaces formed on the first and second jaws of the clip by the beveled surface formed in the leading end of the marker.

Without restriction to the particular apparatus of the third embodiment, the method steps of the third embodiment include the steps of forming a marker of generally cylindrical configuration so that it has a leading end and a trailing end, forming a first bore in the trailing end of the marker in coincidence with a longitudinal axis of symmetry of the marker, forming a second bore in the leading end of the marker in coincidence with a longitudinal axis of symmetry of the marker, forming the first and second bores so that they are in open communication with one another and so that the second bore has a diameter greater than a diameter of said first bore, providing a clip having a trailing end and a leading end, and adapting the trailing end so that it is received within the second bore formed in the leading end of the marker, forming a third bore in the trailing end of the clip marker in coincidence with a longitudinal axis of symmetry of the clip and forming the third bore so that it is cross-shaped in transverse cross-section, providing an inner plunger having a leading end with a circular transverse cross-section of predetermined extent and a pointed distal end of predetermined extent that is adapted to penetrate tissue, the pointed distal end being formed integrally with said the leading end and being positioned in leading relation thereto, providing the inner plunger with a trailing end having a circular transverse cross-section, providing the inner plunger with a middle part having a cross-shaped transverse cross-section that is adapted to be slidingly received within the cross-shaped third bore, forming an outer plunger with a central bore adapted to slidingly receive the trailing end of the inner plunger, providing the outer plunger with a leading end adapted to abuttingly engage the trailing end of the marker, forming a first radially-outwardly extending protuberance on a first jaw of the clip and forming a second radially-outwardly extending protuberance on a second jaw of the clip, forming a first beveled trailing surface on a trailing side of the first protuberance and forming a second beveled trailing surface on a trailing side of the second protuberance, driving the first and second opposed jaws toward one another by driving the marker in a trailing-to-leading direction with the outer plunger so that the leading end of the marker slideably engages the first and second beveled trailing surfaces and drives the first and second beveled trailing surfaces toward one another, the middle part of the inner plunger being positioned on a trailing side of the third bore and the middle part being rotationally misaligned with the cross-shaped third bore so that a trailing end of the middle part is disposed in abutting relation to a leading end of the third bore, the inner plunger being held against movement in a longitudinal direction, thereby holding the clip against movement in said longitudinal direction, so that when the outer plunger is displaced in a trailing-to-leading direction to drive the marker and the clip in said trailing-to-leading direction, the marker leading end enters into sliding engagement with the first and second beveled surfaces and drives them into converging relation with one another. Respective leading ends of the opposed jaws are driven into tissue by continued trailing-to-leading displacement of the outer plunger so that when the jaws are fully embedded within the tissue, a part of the tissue is captured between the jaws. Longitudinal displacement of the inner plunger in a trailing-to-leading direction and rotation of the inner plunger about its longitudinal axis of symmetry until the middle part aligns with the cross-shaped cross section of the third bore, followed by retraction of the inner plunger in a leading-to-trailing direction until the inner plunger has exited the first bore leaves the clip secured to the tissue and the marker secured to the trailing end of the clip.

In the fourth embodiment, an annular bevel is formed in the leading end of the marker to facilitate sliding engagement of the leading end of the marker and the first and second beveled trailing surfaces formed in the first and second jaws, respectively.

A fifth embodiment includes a marker having an elongate cylindrical structure. A cross-shaped bore is formed in the marker by a first slot that intersects with a second slot. The first slot has a greater radial extent than the second slot.

A clip has opposed jaws that are disposed in parallel relation to one another when in a position of repose. The clip has a base fixedly secured to the marker. A cross-shaped bore is formed in the base of the clip by a first slot that intersects with a second slot. The first slot has a greater radial extent than the second slot.

The bore formed in the marker and the bore formed in the base of the clip are in axial alignment with one another.

First and second laterally-outwardly projecting, external wings are formed in the first and second jaws, respectively, and first and second laterally-inward projecting, internal wings are formed in the first and second jaws, respectively. The first and second external wings are diametrically opposed to one another and the first and second internal wings are also diametrically opposed to one another. The first and second external wings have a swept back configuration to facilitate their entry into tissue.

A plunger having a pointed leading end and a cross-shaped transverse cross section that corresponds to the respective shapes of the slots is formed in the marker. The plunger is sequentially inserted into the bore formed in the marker and the bore formed in the trailing end of the clip so that the pointed distal end of the plunger is introduced into a space between the opposed jaws.

The plunger has protuberances that bear against the beveled trailing surfaces formed in the internal wings and cause the opposed jaws to diverge from one another. Accordingly, retracting the plunger so that it disengages from the slots formed in the clip, followed by rotating the plunger ninety degrees to align its radially extending protuberances with the slots, and sequentially pulling the plunger out of the clip and marker enables the opposed jaws to close under an inherent bias. The jaws capture tissue therebetween when so closed. The beveled surfaces serve to engage the tissue and work in conjunction with the external wings to prevent retraction of the clip from the tissue. The first and second external wings prevent reverse migration of the clip after the clip has penetrated the tissue.

Without limiting the fifth embodiment to the particular structure employed, the novel method of the fifth embodiment includes the steps of providing a marker having an elongate cylindrical structure, forming a cross-shaped bore in the marker by forming a first slot that intersects with a second slot, the first slot having a greater radial extent than the second slot, providing a clip having opposed jaws that are disposed in parallel relation to one another when in a position of repose, fixedly securing a base of the clip to the marker, forming a cross-shaped bore in the base of the clip by forming a first slot that intersects with a second slot, said first slot having a greater radial extent than the second slot, positioning the bore formed in the marker and the bore formed in the base of the clip so that the bores are in axial alignment with one another, forming first and second laterally-outwardly projecting, external wings in the first and second jaws, respectively, and forming a first and second laterally-inward projecting, internal wings in the first and second jaws, respectively, positioning the first and second external wings in diametrically opposed relation to one another and positioning the first and second internal wings in diametrically opposed relation to one another, forming the first and second external wings so that they have a swept back configuration to facilitate their entry into tissue, providing a plunger having a pointed leading end and a cross-shaped transverse cross section that corresponds to the respective shapes of the slots formed in the marker, sequentially inserting the plunger into the bore formed in the marker and the bore formed in the trailing end of the clip so that the pointed distal end of the plunger is introduced into a space between the opposed jaws. The plunger protuberances bear against the beveled trailing surfaces formed in the internal wings and thereby cause the opposed jaws to diverge from one another. Retracting the plunger so that it disengages from the slots formed in the clip, followed by rotating the plunger ninety degrees to align the radially extending protuberances of the plunger with the slots, and sequentially pulling the plunger out of the clip and marker enables the opposed jaws to close under an inherent bias. The jaws capture tissue therebetween when so closed. The beveled surfaces serve to engage the tissue and work in conjunction with the external wings to prevent retraction of the clip from the tissue. Moreover, the first and second external wings prevent reverse migration of the clip after the clip has penetrated the tissue.

The apparatus of the sixth embodiment of this invention includes a clip having a base received within a blind cylindrical bore formed in a leading end of a marker. The base is fixedly secured within the bore. The clip includes a pair of opposed jaws that are disposed in substantially parallel relation to one another when in repose. A first pair of recesses is formed in a leading end of a main body of the clip in diametrically opposed relation to one another. A second pair of recesses is formed in the trailing end of the main body of the clip, each recess of said pair of recesses being disposed in diametrically opposed relation to the other recess. A pair of diametrically opposed raised areas is formed in the main body between the recesses.

The clip is ensleeved within a delivery catheter and the delivery catheter is ensleeved within a cylindrical sleeve. A pair of diametrically opposed, radially inwardly extending pins are formed in the cylindrical sleeve. A first opening is formed in the delivery catheter to accommodate a first pin and a second opening is formed in the delivery catheter in diametric opposition to the first opening to accommodate a second pin. A leading end of the delivery catheter and a leading end of the cylindrical sleeve are in substantial alignment with one another and the opposed jaws are in repose when the cylindrical sleeve is positioned in ensleeving relation to the delivery catheter and hence to the clip.

Advancing the plunger in a trailing-to-leading the direction causes the marker to drive the clip in the same direction and causes the opposed jaws to be driven toward one another because the pins are constrained against radial travel by the cylindrical sleeve and because the pins cannot be displaced in a radially outward direction when they are compelled to slide out of the leading recesses onto the respective raised surfaces formed in the main body. The respective distal free ends of the jaws firmly grasp tissue therebetween, permanently anchoring the clip to the tissue.

Continued advancement of the plunger enables the pins to slide from the respective raised surfaces into engagement with the trailing recessed surfaces, thereby releasing pressure form the pins and enabling withdrawal of the delivery catheter and cylindrical sleeve.

Without limitation to the structure of the sixth embodiment, the sixth novel method includes the steps of forming a blind cylindrical bore in a leading end of a cylindrical marker, providing a clip having a base received within the blind cylindrical bore, providing the clip with a pair of opposed jaws that are disposed in substantially parallel relation to one another when in repose, forming a first pair of recesses in a main body of the clip in diametrically opposed relation to one another, forming a second pair of recesses in the trailing end of the main body of the clip in diametrically opposed relation to one another, thereby forming a pair of diametrically opposed raised areas in said main body between the leading and trailing recesses, forming a pair of diametrically opposed, radially inwardly extending pins in a cylindrical sleeve that ensleeves a delivery catheter that ensleeves said clip, forming a first opening in said delivery catheter to accommodate a first pin and forming a second opening formed in the delivery catheter in diametric opposition to the first opening to accommodate a second pin, positioning a leading end of the delivery catheter and a leading end of the cylindrical sleeve in substantial alignment with one another so that advancing a plunger introduced into a trailing end of a lumen of said delivery catheter in a trailing-to-leading direction causes the marker to drive the clip in the same direction and causes the opposed jaws to be driven toward one another because the pins are constrained against radial travel by the cylindrical sleeve and because the pins cannot be displaced in a radially outward direction when they are compelled to slide out of the leading recesses onto the raised surfaces formed in said main body. The respective distal free ends of the jaws firmly grasp tissue therebetween, permanently anchoring the clip to the tissue. Continued advancement of the plunger displaces the clip until the pins in the cylindrical sleeve enter into registration with the recesses formed in the trailing end of the main body of the clip, thereby releasing pressure from the pins and enabling leading-to-trailing retraction of the delivery catheter and cylindrical sleeve.

In a seventh embodiment, a core biopsy needle is employed but no vacuum is required to pull tissue into the lumen of the delivery catheter. In the apparatus of the seventh embodiment, a core biopsy needle has a side port near a leading end thereof and a delivery catheter has a side port near a leading end thereof. The delivery catheter is slideably disposed within a lumen of the core biopsy needle. The side port of the delivery catheter is in substantial juxtaposition with the side port of the core biopsy needle.

A ramp member is disposed at a leading end of the delivery catheter and includes an arcuate curved surface formed in a trailing end thereof.

A marker is disposed in a lumen of the delivery catheter. An attachment means has a trailing end secured to the marker and a leading end disposed in leading relation thereto. A barb means for engaging tissue is formed in the leading end of the attachment means.

A plunger is disposed in the lumen of the delivery catheter in trailing relation to the marker. The plunger is adapted to push the marker into the ramp member so that the attachment means is pushed through the delivery catheter side port and the core biopsy needle side port so that the barb means formed in the leading end of the attachment means is embedded within tissue that surrounds the core biopsy needle.

The marker is secured to the tissue when it has been pushed from the delivery catheter and the barb maintains the marker against migration in the absence of a vacuum means for pulling tissue into the core biopsy needle or the delivery catheter.

An important object of this invention is to provide a marker and a clip adapted to non-releasably engage tissue where the marker and clip are formed integrally with one another.

Another object is to provide a marker and clip that are not formed integrally with one another but which become conjoined to one another at the time of a tissue site is marked.

Another object is to provide a marker having a clip or other attachment means of the type that may be delivered to a tissue site by a core biopsy needle of the type that employs a vacuum, a core biopsy needle of the type that does not employ a vacuum, and by a coaxial biopsy needle.

Additional objects include the provision of multiple methods for using the several structural embodiments of the invention.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 9 is the second view of said seven step animation;

FIG. 10 is the third view of said seven step animation;

FIG. 11 is the fourth view of said seven step animation;

FIG. 12 is the fifth view of said seven step animation;

FIG. 13 is the sixth view of said seven step animation;

FIG. 14 is the seventh view of said seven step animation;

FIG. 17 is a side elevational view depicting the plunger of FIG. 15 slideably inserted within a bore formed in the marker of FIG. 16 and extending into the clip of FIG. 16;

FIG. 18 is a side elevational view like that of FIG. 17, depicting the plunger when fully advanced;

FIG. 19 is a side elevational view of a fourth embodiment of the bioabsorbable marker and clip;

FIG. 20 is a perspective view of a fifth embodiment;

FIG. 21 is a top plan view of the parts depicted in FIG. 19;

FIG. 24 is a side elevational view depicting the marker and clip after the plunger is retracted, rotated ninety degrees, and withdrawn from the marker and clip assembly;

FIG. 25 is a side elevational view depicting the marker and clip assembly of a fifth embodiment when the plunger is fully withdrawn and with the clip attached to tissue;

FIG. 28 depicts the parts of FIG. 27 when the plunger is rotated ninety degrees (90°) preparatory to being pulled out of the marker/clip assembly;

FIG. 29 depicts the marker/clip when the clip is locked onto a piece of tissue;

DETAILED DESCRIPTION

Figure 1:
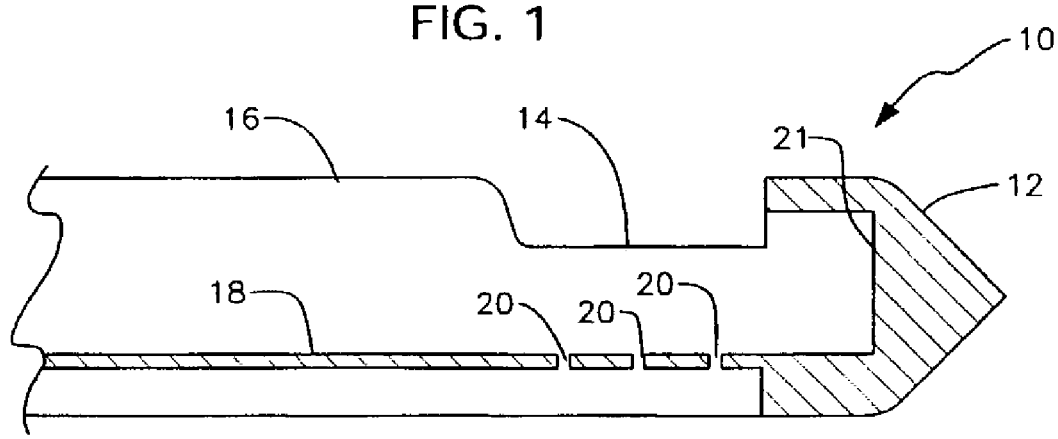
FIG. 1 is a sectional side elevational view of a commercially available needle.

Referring to the longitudinal sectional view of FIG. 1, it will there be seen that the reference numeral 10 denotes a prior art needle sold under the trademark Mammotone® core biopsy needle. This invention has utility in connection with all core biopsy needles, of which the Mammotone® core biopsy needle is merely an example.

However, some core biopsy needles do not employ a vacuum as does the Mammotone® core biopsy needle. As will be disclosed later in this disclosure, this invention also has utility in connection with such vacuumless core biopsy needles.

Moreover, this invention also has utility in connection with coaxial biopsy needles, as disclosed in greater detail near the end of this disclosure. Coaxial biopsy needles do not employ a vacuum to pull tissue into a lumen thereof.

Core biopsy needle 10 is of the vacuum type as aforesaid and has a solid, pointed leading end 12. A side-opening port 14 is formed in cylindrical sidewall 16 of the needle in slightly trailing relation to said leading end 12.

Figure 1A:
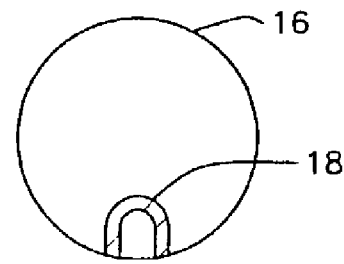
FIG. 1A is an end view of the needle depicted in FIG. 1.

As best understood when comparing FIGS. 1 and 1A, a vacuum lumen 18 is formed along the extent of needle 12 and a plurality of openings, collectively denoted 20, are formed in vacuum lumen 18 near its leading end in diametrically opposed relation to sideport 14.

Cavity 21 is formed in solid leading end 12, in leading relation to sideport 14.

Figure 2:
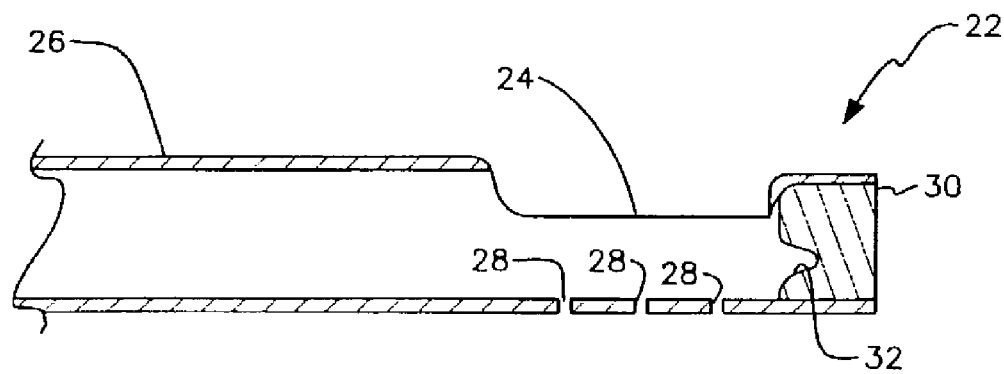
FIG. 2 is a sectional side elevational view of a delivery catheter having a novel anvil received within the leading end of the lumen of said delivery catheter.

FIG. 2 depicts a novel delivery catheter 22 having side port 24 formed in cylindrical sidewall 26. A plurality of openings, collectively denoted 28, are formed in sidewall 26 in diametrically opposed relation to sideport 24.

Anvil 30 is fixedly secured to the leading end of delivery catheter 22 as depicted, and includes cavity 32 formed therein. Anvil 30 is made of a hard material, preferably metal. Cavity 32 is a blind bore formed in the center of anvil 30; it has a gently rounded concave bottom.

Figure 3:
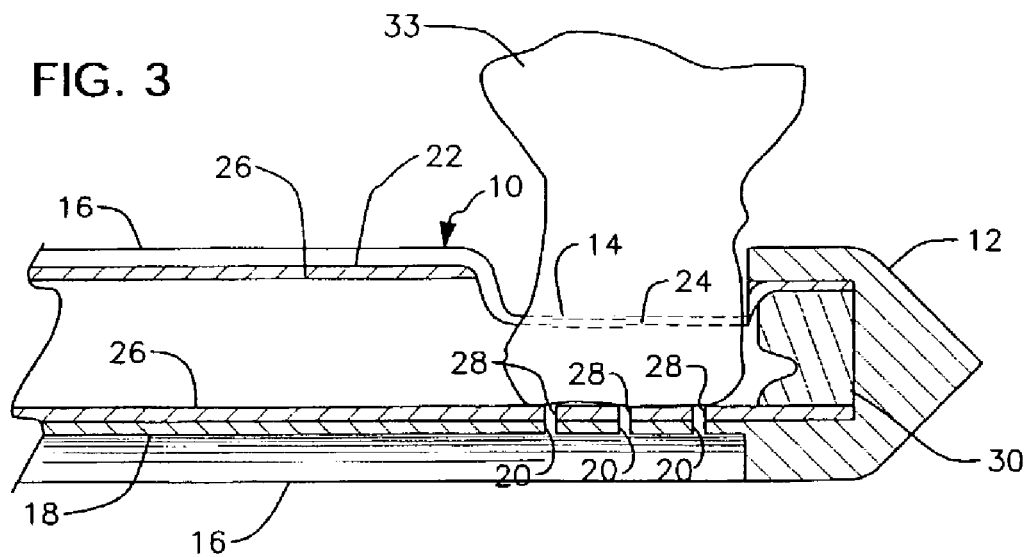
FIG. 3 is a sectional side elevational view depicting the delivery catheter and anvil of FIG. 2 positioned within the lumen of the needle of FIG. 1.

FIG. 3 depicts delivery catheter 22 of FIG. 2 when slidingly disposed within core biopsy needle 10 of FIG. 1. Sideports 14 and 24 are in substantial juxtaposition with one another, as are openings 20 and 28, and anvil 30 is fully received within cavity 21. A vacuum has been applied to vacuum lumen 18 and the alignment of openings 20 and 28 has caused part of a lesion, tumor, cyst, or other form of tissue 33 to be pulled into sideports 14 and 24 so that it is positioned within the hollow interior of delivery catheter 22.

Figure 4:
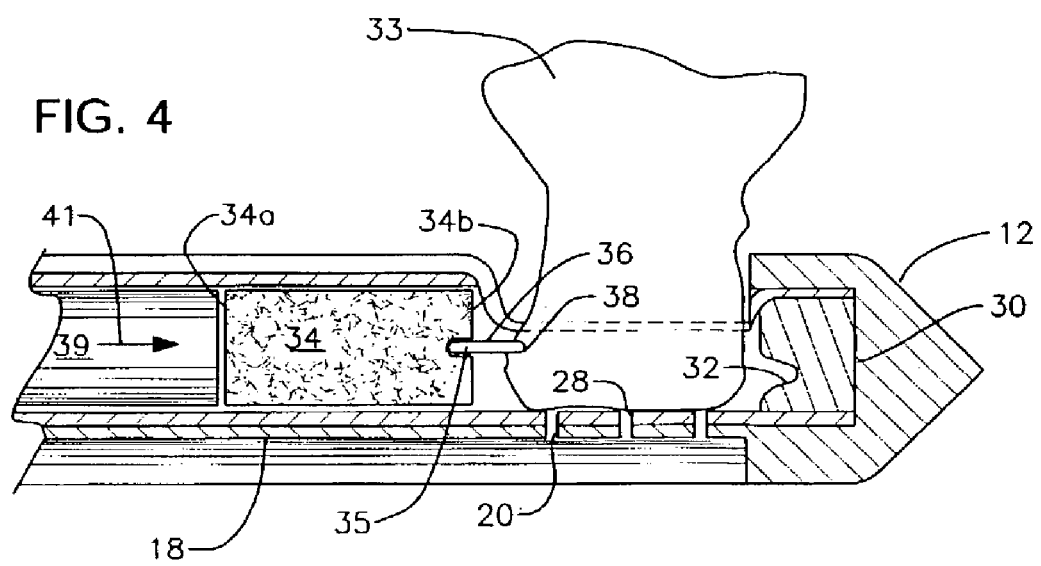
FIG. 4 is a sectional side elevational view depicting the novel marker and a plunger positioned within the lumen of said delivery catheter.

FIG. 4 depicts a bioabsorbable marker 34 disposed within the hollow interior of delivery catheter 22. The trailing end of marker 34 is denoted 34a and its leading end is denoted 34b. It should be understood that this invention also relates to markers that are not bioabsorbable. A trailing end 35 of straight member 36 of metallic construction is embedded within leading end 34b of marker 34 as depicted. As drawn, pointed leading end 38 of straight member 36 has penetrated into tissue 33 because plunger 39 has been introduced into the open trailing end of delivery catheter 22 and displaced in a trailing-to-leading direction, denoted by single-headed directional arrow 41, so that it abuts trailing end 34a of marker 34 and drives it forward.

Figure 5:
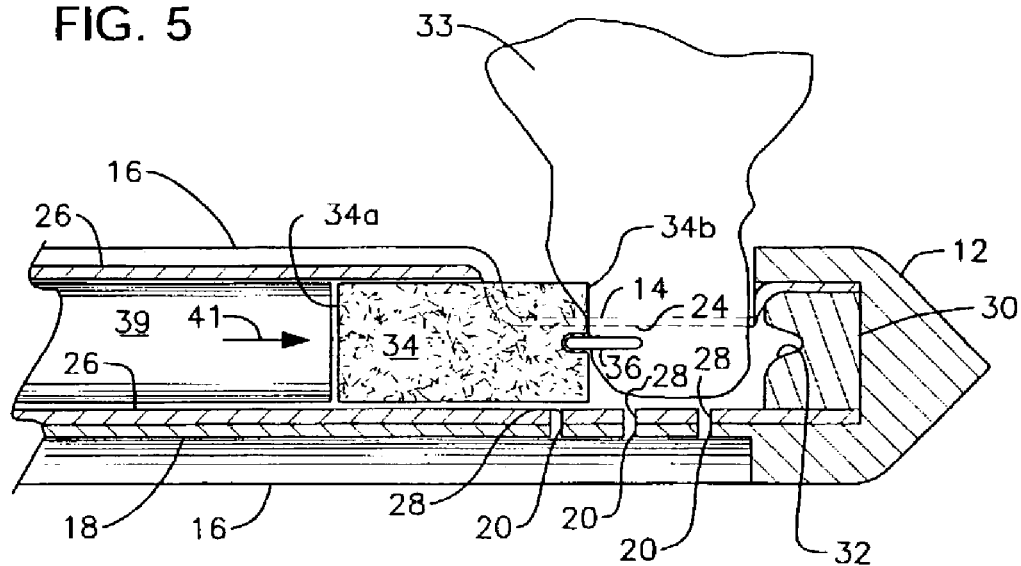
FIG. 5 is a view like that of FIG. 4, depicting the novel marker and plunger when the plunger has been advanced relative to its FIG. 4 position.

Plunger 39 has been further advanced in the direction of arrow 41 in FIG. 5, straight member 36 has advanced deeper into tissue 33, and tissue 33 has been confined into a relatively small space at the leading end of sideports 14, 24.

Figure 6:
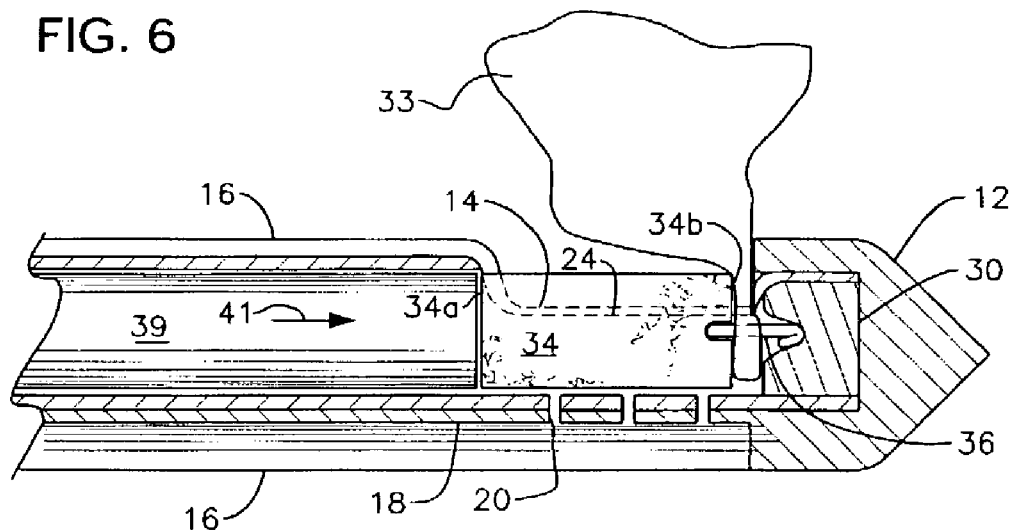
FIG. 6 is a view like that of FIG. 5, depicting the novel marker and plunger when the plunger has been advanced relative to its FIG. 5 position.

In FIG. 6, plunger 39 has been advanced still further in the direction of arrow 41 and straight member 36 has pierced tissue 33. Pointed leading end 38 of straight member 36 has been shoved into cavity 32 and bent back as depicted by its rounded concave bottom to form a hook.

Figure 7:
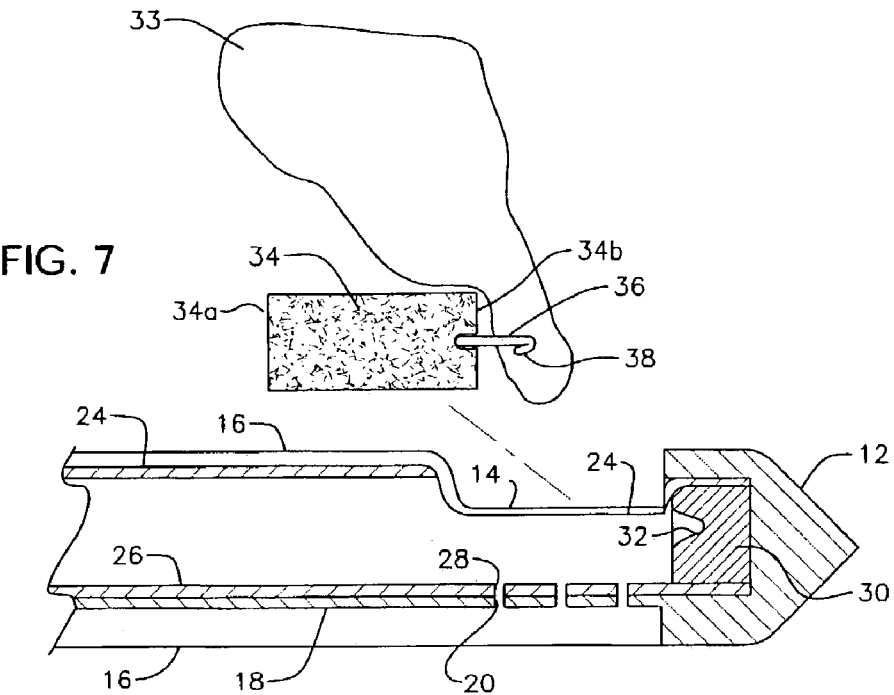
FIG. 7 depicts the parts depicted in FIG. 6 after the novel marker has been removed from the needle.

The vacuum in vacuum lumen 18 is then turned off so that tissue 33 may be withdrawn from sideports 14 and 24 as depicted in FIG. 7. Bioabsorbable marker 34 exits through sideports 14 and 24 with lesion 33 because it is now hooked to said lesion as depicted.

A second embodiment is depicted in FIGS. 8–14. Core biopsy needle 10 and delivery catheter 22 are also used in this embodiment, but said parts are not depicted to simplify the drawings.

Metallic straight member 36 of the first embodiment is replaced in this second embodiment by clip 40 that is permanently bonded by suitable means to bioabsorbable marker 34. Specifically, clip 40 has an annular base 42 that is received within an annular cavity 44 formed in leading end 34b of marker 34. A central bore 46 is formed in marker 34 in coincidence with its longitudinal axis of symmetry and a similar bore 48 is formed in annular base 42 of clip 40 so that bores 46 and 48 are in axial alignment with one another when the trailing end of clip 40 is secured to the leading end 34b of marker 34.

Clip 40 is preferably of metallic construction but may also be made of other materials as mentioned above.

Figure 8:
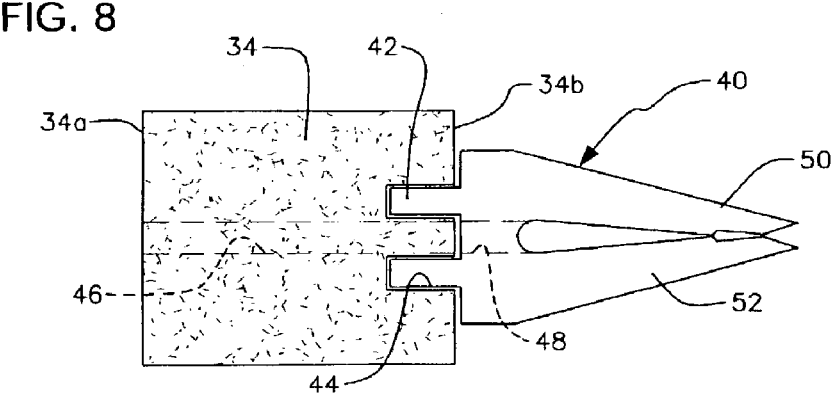
FIG. 8 is the first view of a seven step animation depicting the installation of a second embodiment of the novel marker in a tissue or lesion.

The FIG. 8 configuration of clip 40 is its in repose, normally closed configuration where opposed jaws 50, 52 are disposed in converging relation to one another.

As depicted in FIG. 9, plunger 54 has an elongate extension 56 formed at its leading end that terminates at a sharp distal end 58. The leading end of the main body of plunger 54 is denoted 55. Said leading end 55 is adapted to bear against trailing end 34a of marker 34. Elongate extension 56 is introduced sequentially through central bore 46 and central bore 48 until said distal end 58 is positioned between jaws 50 and 52 of clip 40.

Jaws 50, 52 assume their fully open position when plunger 54 and hence elongate extension 56 are fully advanced as depicted in FIG. 10. Note that sharp point 58 now extends beyond the respective leading ends of jaws 50, 52 and is poised to penetrate tissue 33. Leading end 55 of plunger 54 abuts trailing end 34*a* of marker 34 when plunger extension 56 is fully inserted between jaws 50, 52.

FIG. 11 depicts the initial penetration of tissue 33 by clip 40 and FIG. 12 depicts clip 40 when fully seated within said tissue 33.

Partial retraction of plunger 54 and hence of plunger extension 56 is depicted in FIG. 13. Clip 40 is formed of a flexible and resilient metal so that normally closed jaws 50, 52 converge toward one another under their inherent bias when plunger extension 56 is withdrawn from between said jaws as shown. A part of tissue 33 is captured between said jaws when the jaws converge, thereby anchoring clip 40 to said tissue.

FIG. 14 depicts full retraction of plunger 54. Bioabsorbable marker 34 remains fixedly secured to clip 40 and clip 40 remains clamped onto tissue 33. Accordingly, even after marker 34 has been bioabsorbed, if it is made of bioabsorbable materials, clip 40 will continue to permanently mark the site and said clip will not migrate therefrom.

A third embodiment is depicted in FIGS. 15–22. This embodiment is the only embodiment where the marker and the metal hook are manufactured separately and do not combine with one another until a site is marked. This embodiment is also the only embodiment having two plungers, hereinafter referred to as the inner and outer plungers.

Figure 15:
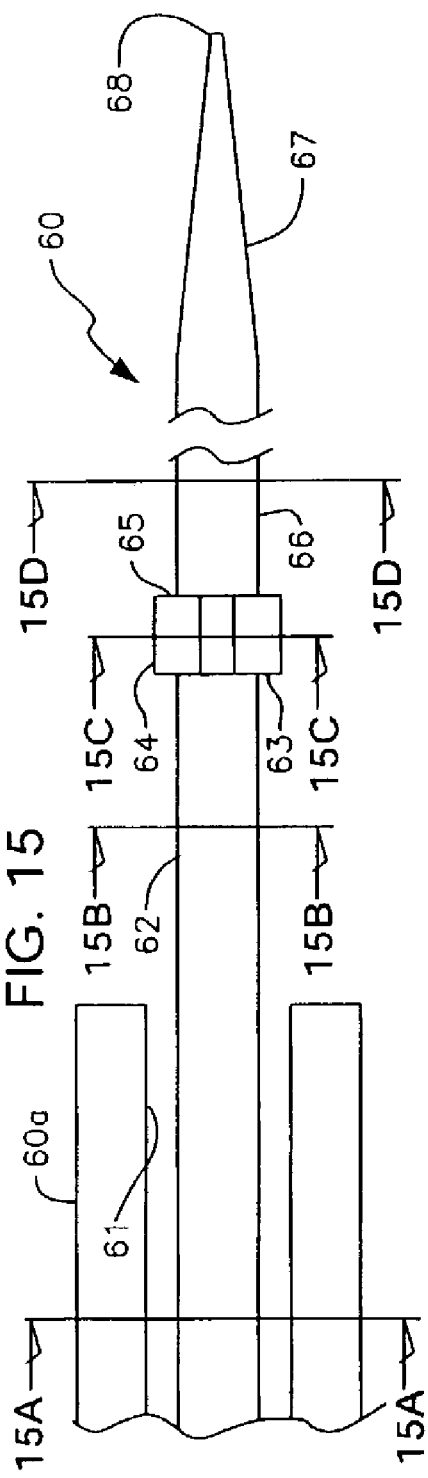
FIG. 15 is a side elevational view of a plunger that forms a part of the third embodiment.

As depicted in FIG. 15, inner plunger 60 has a trailing section 62 of a first diameter, a leading section 66 of the same diameter as said trailing section, a middle section 64 having an enlarged diameter relative to trailing section 62 and leading section 66, and a tapered leading section 67 that terminates in sharp point 68. Annular step 63 is formed where section 62 meets section 64, and annular step 65 is formed at the juncture of sections 64 and 66.

Outer plunger 60*a* is of cylindrical configuration and has a central bore 61 that accommodates trailing section 62 of inner plunger 60. Accordingly, inner plunger 62 is concentrically disposed with respect to outer plunger 60*a* as indicated in the transverse cross sectional view of FIG. 15A. The transverse cross section of inner plunger 62 is circular as depicted in FIG. 15B, the transverse cross section of middle section 64 is cross-shaped as depicted in FIG. 15C, and the transverse cross section of leading section 66 of inner plunger 62 is circular as depicted in FIG. 15D.

Figure 16A:
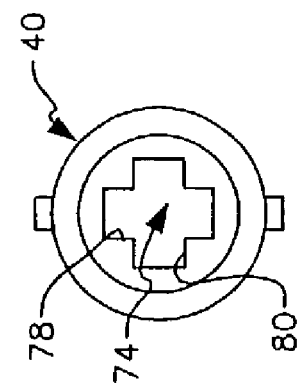
FIG. 16A is a rear perspective view of the clip of the third embodiment.
Figure 16:
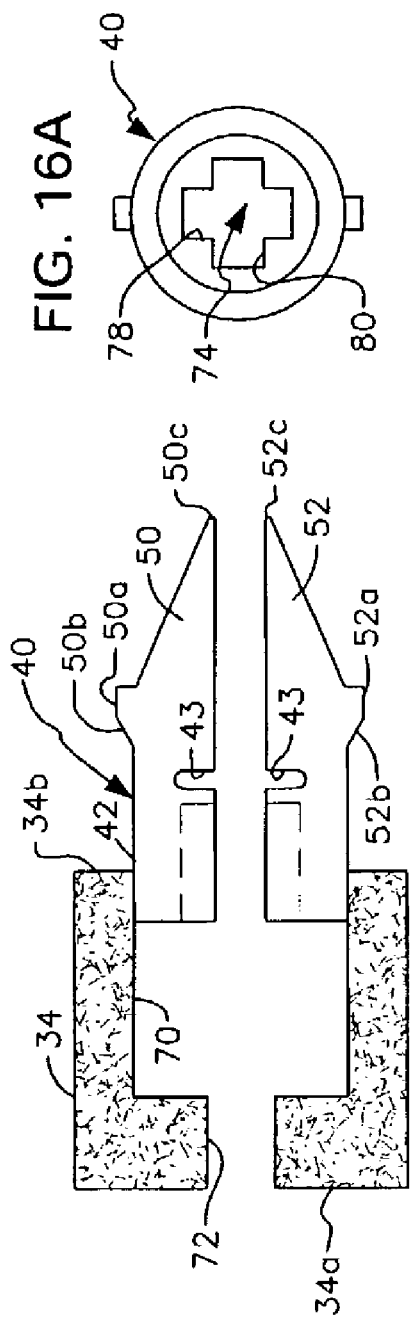
FIG. 16 is a side elevational view of the marker and clip of the third embodiment.

FIG. 16 depicts the structure of bioabsorbable marker 34 and clip 40 of this embodiment, and FIG. 16A depicts the proximal or trailing end of clip 40. A cross shaped bore 74 is formed by the intersection of elongate slot 78 and truncate slot 80. The terms "elongate" and "truncate" indicate that slot 78 has a greater radial extent than does slot 80. The transverse cross section of middle part 64 (FIG. 15C) matches said cross shaped bore 74. Specifically, middle part 64 has a radially long protrusion 64*a* and a radially short protrusion 64*b*, said protrusions extending along the longitudinal extent of said part. Thus, if radially long and short protrusions 64*a*, 64*b* are rotationally aligned with radially long and short slots 78, 80 of bore 74, respectively, then middle part 64 may slideably enter into the hollow interior of the trailing end of clip 40. Plunger parts 62 and 64 are circular in cross section as aforesaid and enter into the hollow interior of clip 40 regardless of the rotational orientation of inner plunger 60.

In this embodiment, cylindrical cavity 70 is formed in leading end 34*b* of cylindrical marker 34 as indicated in FIG. 16. Bore 72 is formed in trailing end 34*a* of marker 34, in coincidence with its longitudinal axis of symmetry. Long and short slots 78, 80 formed in clip 40 collectively form cross-shaped bore 74 as aforesaid and bores 72, 74 are in axial alignment with one another when trailing end 42 of clip 40 is slideably received within cylindrical cavity 70.

Significantly, marker 34 and clip 40 are independently manufactured and form separate and distinct parts that are unconnected to one another. Clip 40 is positioned so that its trailing end is slideably received within cavity 70 of marker 34 as aforesaid. As will become clear as this disclosure proceeds, said two parts effectively become a single part when the site-marking process has been concluded.

FIG. 16 also depicts beveled surfaces 50*b*, 52*b* formed on the trailing side of protrusions 50*a*, 52*a*, respectively, formed in each jaw 50, 52 of clip 40. The function of beveled annular surfaces 50*b*, 52*b* will become clear as this description proceeds.

Notches 43 formed in each jaw of clip allow the respective distal or leading tips 50*c*, 52*c* of each jaw to converge toward one another as will also become clear as this description proceeds.

The manner in which the parts depicted in FIGS. 15, 16, and 16A work with one another is best understood in connection with FIGS. 17–22. In FIG. 17, inner plunger 60 is sequentially introduced through bore 61 formed in outer plunger 60*a*, bore 72 formed in marker 34, and bore 74 formed in the trailing end of clip 40 until cross-shaped middle section 64 of inner plunger 60 is received within cross-shaped bore 74 of clip 40. This introduction is accomplished while middle section 64 is held in rotational alignment with slots 78 and 80 formed in the trailing end of clip 40.

Next, inner plunger 60 is pushed forward (in the direction of single-headed directional arrow 59) so that middle section 64 is positioned in distal relation to notches 43, 43 as depicted in FIG. 18. Cross-shaped bore 74 does not extend to the part of clip 40 that is distal of said notches 43, 43. More particularly, the space denoted 74*a* is the space between jaws 50, 52 of clip 40 and as such is not a bore. Nor does cross-shaped bore 74 extend from the trailing end of clip 40 to said notches; it extends about half of said length. The area marked 74*a* in FIG. 18 has a circular cross section. Thus it should be understood that cross-shaped bore 74 extends from the trailing end of clip 40 to a point about mid-way between said trailing end and notches 43, 43.

Inner plunger 60 is rotated ninety degrees (90°) about its longitudinal axis of symmetry after it has attained its FIG. 18 position. Such rotation causes the radially long and radially short protrusions formed in middle section 64 of inner plunger 60 to misalign with long and short slots 78, 80, respectively.

Inner plunger 62 is then withdrawn in a direction opposite to that of directional arrow 59 until it reaches its FIG. 19 position. When in said FIG. 19 position, the misalignment of the radially long and radially short protrusions formed in middle section 64 with long and short slots 78, 80, respectively, prevents further retraction of said inner plunger 62. Specifically, annular shoulder 63 at the trailing end of middle section 64 abuts bore 74 in misalignment therewith. Accordingly, with middle section 64 in its FIG. 19 position, and with inner plunger 60 held against movement by a physician, advancing outer plunger 60*a* and hence marker 34 in the direction indicated by directional arrow 59 causes marker 34 to advance in the direction indicated by directional arrow 59, thereby driving the trailing end of clip 40 deeper into cavity 70 of marker 34, as indicated in FIG. 20.

Figures 20, 21:
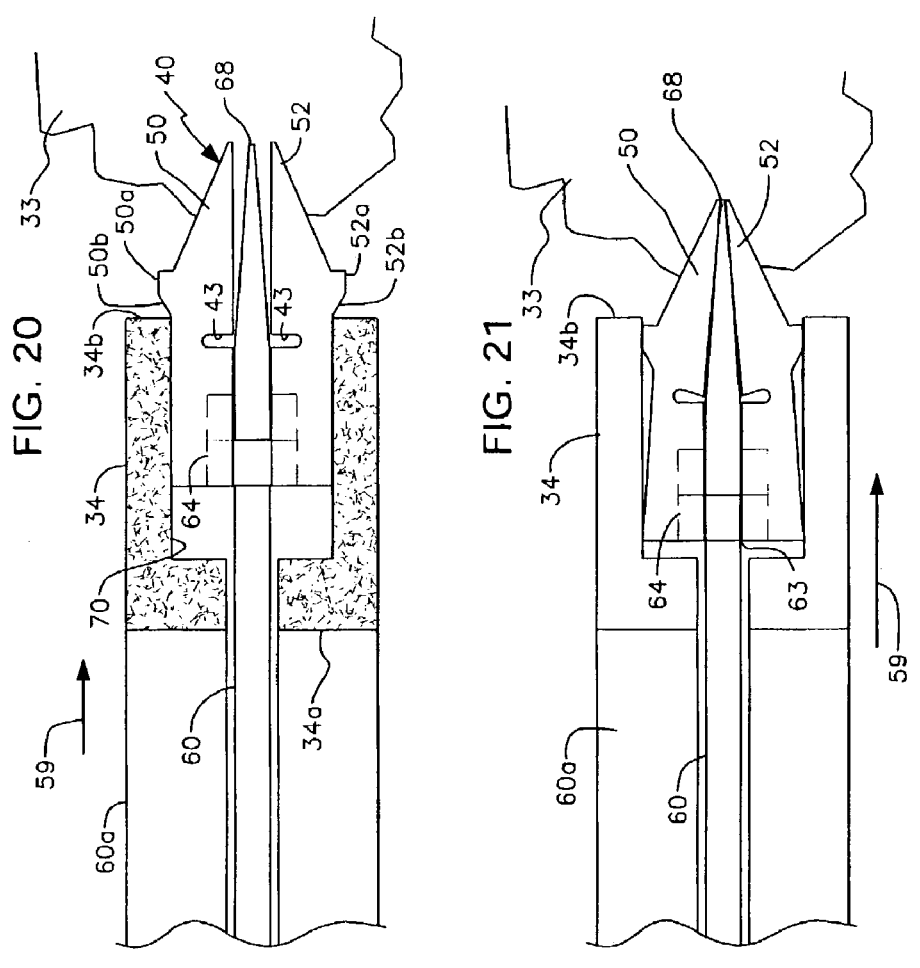

As outer plunger 60*a* and marker 34 are pushed in the direction of directional arrow 59, clip 40 begins to penetrate tissue 33 as also depicted in FIG. 20. Note that in FIG. 20, leading end 34b of marker 34 is about to make contact with ramps 50b, 52b of protuberances 50a, 52a, respectively, formed in jaws 50, 52 of clip 40.

Further forward travel of outer plunger 60a, as depicted in FIG. 21, thus drives leading end 34b of marker 34 into sliding engagement with said ramps 50b, 52b. Notches 43, 43 create a weakness in jaws 50, 52 so that said jaws converge toward one another as depicted in FIG. 21 as said leading end of marker 34 rides over said ramped surfaces 50b, 52b. When the jaws converge, they capture a quantity of tissue 33 between them as depicted in said FIG. 21. Clip 40 is not made of a resilient material in this embodiment so that when said jaws close onto said tissue, they remain in clamping engagement with said tissue even when marker 34 is bioabsorbed.

Figure 22:
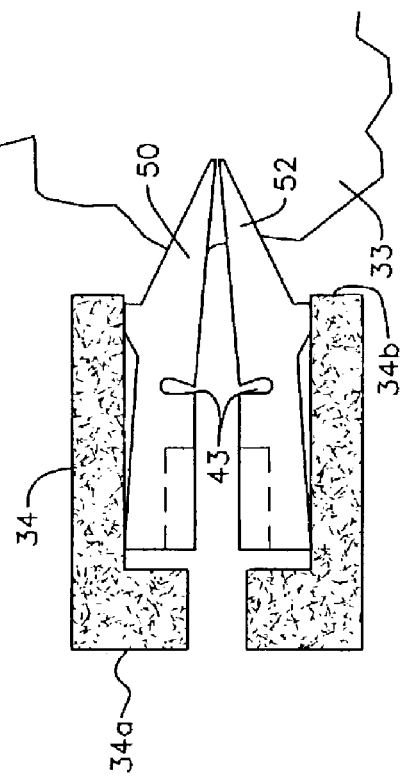
FIG. 22 is a side elevational view of the clip of the fifth embodiment.

FIG. 22 depicts the final position of marker 34 and metal clamp 40 when outer plunger 60a has driven marker 34 and hence clip 40 fully into tissue 33.

FIG. 22 also depicts the assembly after inner plunger 60 and outer plunger 60a have been withdrawn. Such withdrawal is accomplished by advancing inner plunger 60a short distance in the direction of directional arrow 59 (FIG. 21) so that annular trailing shoulder 63 of middle part 64 is positioned forwardly of bore 74. Inner plunger 60 is then rotated ninety degrees (90°) about its longitudinal axis a second time until the radial protuberances formed in said middle part 64 align with long and short slots 78, 80 so that said inner plunger 60 may be withdrawn in a direction opposite to the direction indicated by directional arrow 59.

After bioabsorbable marker 34 has been bioabsorbed over a period of days, weeks, or months, depending upon its composition, clip remains secure to tissue 33. Clip 40 will not migrate with respect to said tissue because its jaws 50, 52 permanently anchor it to said tissue.

Figure 23:
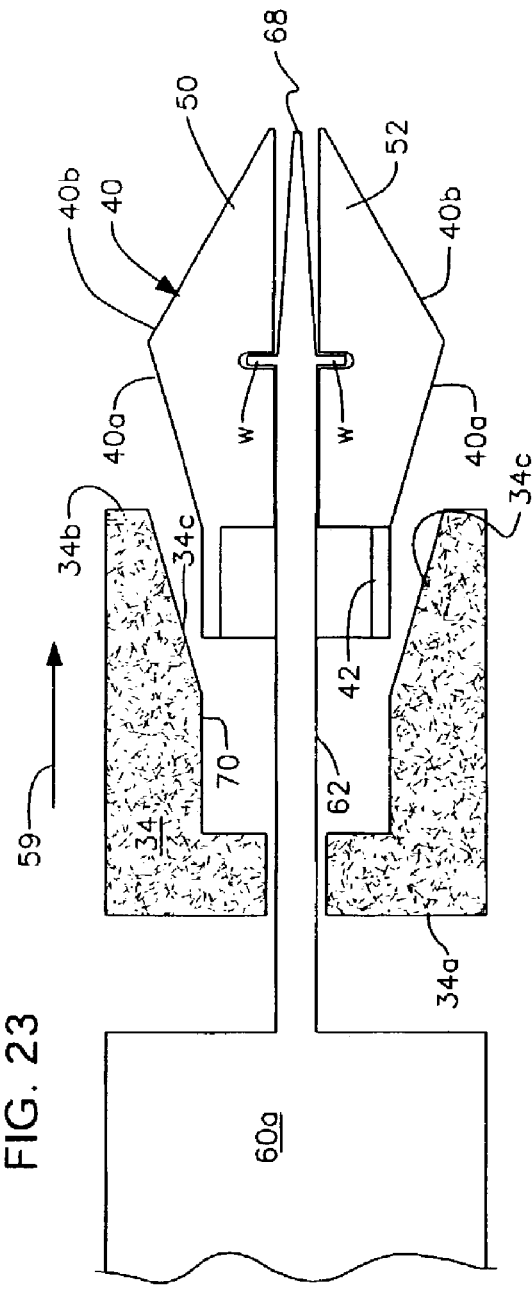
FIG. 23 is a side elevational view of the fifth embodiment when a plunger having a cross-shaped profile is used to open the clip.

A fourth embodiment is depicted in FIG. 23. Beveled annular surface 34c is formed in leading end 34b of marker 34 and is in open communication with blind bore 70. Jaws 50, 52 of clip 40 have beveled trailing surfaces 40a, 40a and beveled leading surfaces 40b, 40b formed therein. In this way, when outer plunger 60a is advanced in a trailing-to-leading direction, denoted by directional arrow 59, beveled annular surface 34c bears against beveled surfaces 40a, 40a, causing jaws 50, 52 of clip 40 to converge toward one another and to pinch tissue 33, not shown, therebetween.

In all other aspects, the fourth embodiment of the invention works in the same way as the structure of the third embodiment.

A fifth embodiment is depicted in FIGS. 24–29. Bioabsorbable marker 34 has an elongate cylindrical structure in this embodiment. Cross-shaped bore 74a is formed in marker 34 by an elongate slot 78 that intersects with a truncate slot 80, just as in the third embodiment in connection with the trailing end of clip 40 of that embodiment. The plunger of the delivery catheter, not depicted in FIG. 24, is slideably received within said slots when this fifth embodiment is in use.

Clip 40 of this embodiment includes opposed jaws 50, 52 that are disposed in parallel relation to one another when in their position of repose.

As best understood in connection with FIG. 25, clip 40 has a base 40a that is fixedly secured to bioabsorbable marker 34. Bore 74a formed in marker 34 has a cross-shaped cross-section because it is formed by the intersection of slots 78 and 80 as aforesaid. Bore 74, formed in base 40a of clip 40 and in the trailing end of said clip as depicted, also has a cross-shaped cross section for the same reason. Bores 74 and 74a are in axial alignment with one another.

Clip 40 has a pair of laterally-outwardly projecting, external wings 82, 84 formed therein and a pair of laterally-inward projecting, internal wings 86, 88 formed therein. External wings 82, 84 are diametrically opposed to one another as are internal wings 86, 88. Said external wings prevent reverse migration of clip 40 during deployment. They are swept back to facilitate their entry into tissue, and such swept back configuration acts as a detent means to prevent retraction thereof from tissue.

Figure 26A:
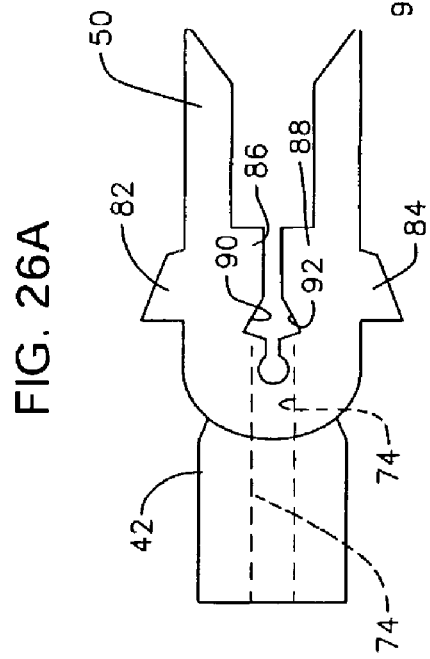
FIG. 26A depicts the clip of the fifth embodiment in its normally closed position.
Figure 27:
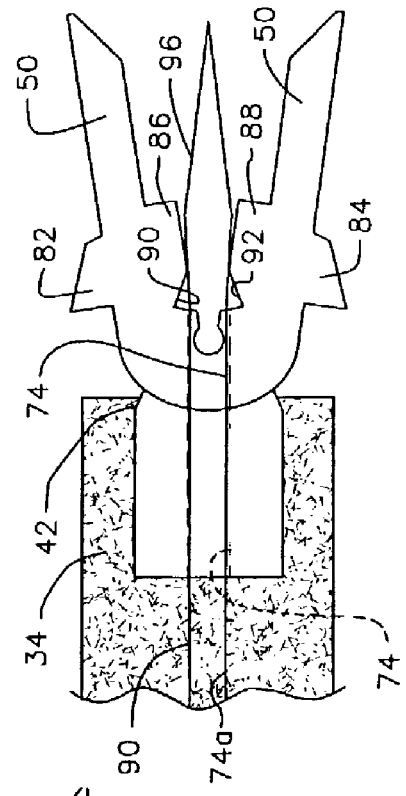
FIG. 27 depicts the marker and clip assembly of the fifth embodiment when the jaws of the clip member are opened by insertion of a plunger having a cross-shaped cross-section.
Figure 26B:
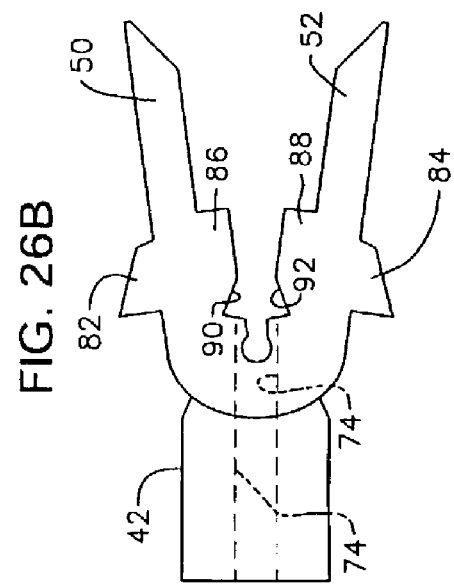
FIG. 26B depicts the clip of FIG. 25 when in its open position.

The closed configuration of clip 40 is depicted in FIG. 26A and its open configuration is depicted in FIG. 26B. Plunger 94, depicted in FIG. 27, having pointed leading end 96, has a cross-shaped transverse cross section that corresponds to the respective shapes of slots 78, 80 which collectively form bore 74a in marker 34. In other words, plunger 94 has a first pair of diametrically opposed, radially extending ribs that correspond to and are slideably received within elongate slots 78 and a second pair of diametrically opposed, radially extending ribs that correspond to and are slideably received within truncate slots 80. The first pair of ribs extends radially outwardly a greater extent than does the second pair of ribs.

Plunger 94 is inserted into marker bore 74a and into bore 74 of clip 40. Pointed end 96 is thereby introduced into the space between opposed jaws 50, 52. As plunger 94 is further advanced, the first pair of ribs bears against beveled surfaces 90, 92 that are formed in the trailing edges of internal wings 86, 88, respectively, causing jaws 50, 52 to diverge from one another in the manner depicted in FIGS. 26B and 27.

As indicated in FIG. 28, plunger 94 is then retracted and rotated ninety degrees (90°) and pulled out of the marker 34/clip 40 assembly. This ninety degree (90°) rotation aligns the radially extending ribs formed in plunger 94 with slots 78, 80 formed in clip 40 so that no resistance is presented to the retraction.

In FIG. 29, jaws 50, 52 have returned to their position of repose where they are in substantial parallelism to one another because plunger 94 has been fully withdrawn, allowing said jaws to re-converge under their inherent bias. Beveled surfaces 90, 92 now serve to engage tissue 33 and work in conjunction with external wings 82, 84 to prevent retraction of said clip 40 from said tissue 33.

Figure 30:
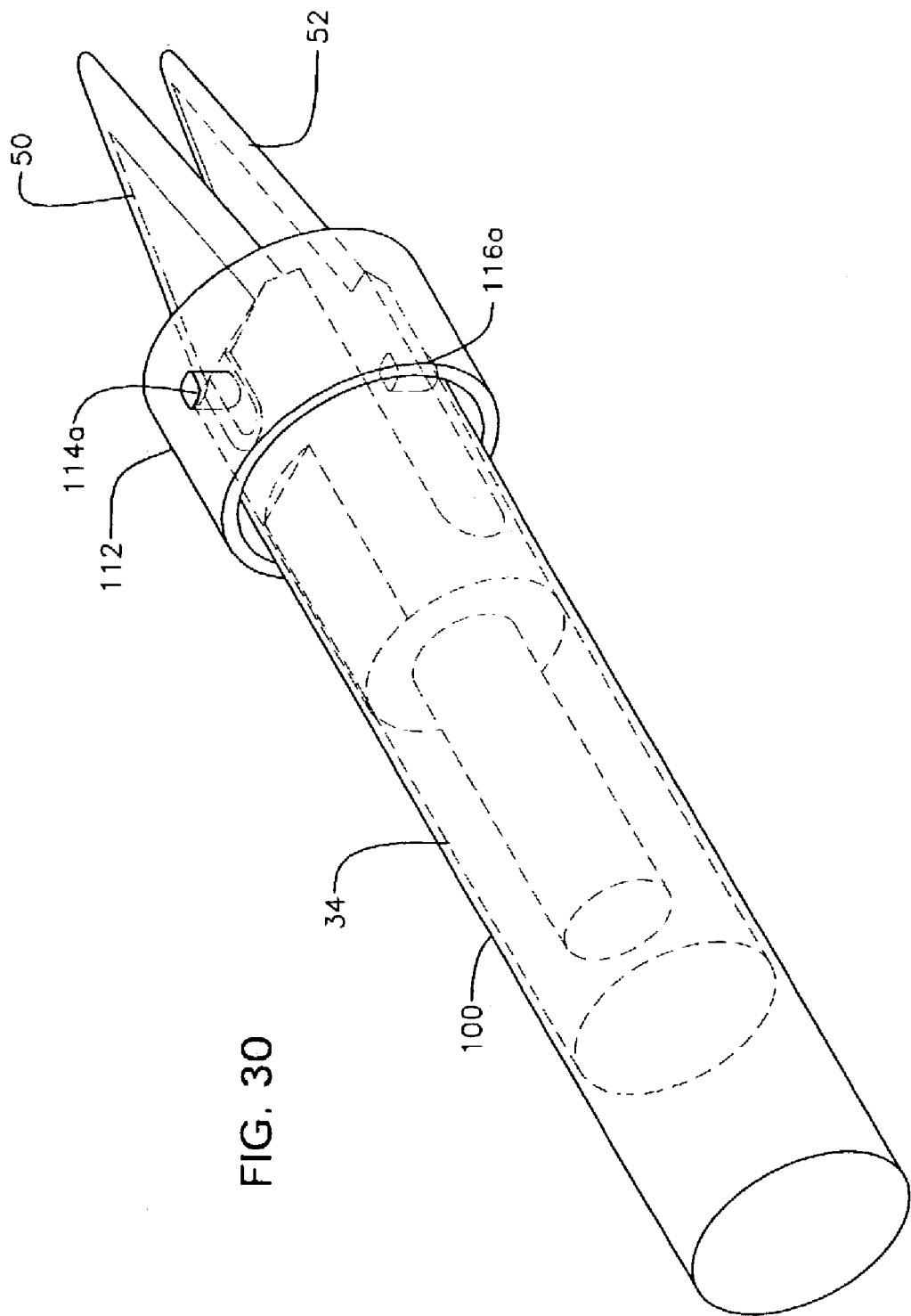
FIG. 30 is a perspective view of a sixth embodiment of the invention.

A sixth embodiment is depicted in perspective view in FIG. 30. It is delivered to the biopsy site by delivery catheter 100. As best understood in connection with FIG. 31 and FIG. 35 which is a longitudinal sectional view taken from FIG. 31, base 42 of clip 40 is received within blind cylindrical bore 102 formed in the leading end of bioabsorbable marker 34 and said base 42 is fixedly secured within said bore. FIGS. 30, 31, 32A, 32B and 35 depict opposed jaws 50, 52 in their position of repose.

Figure 32:
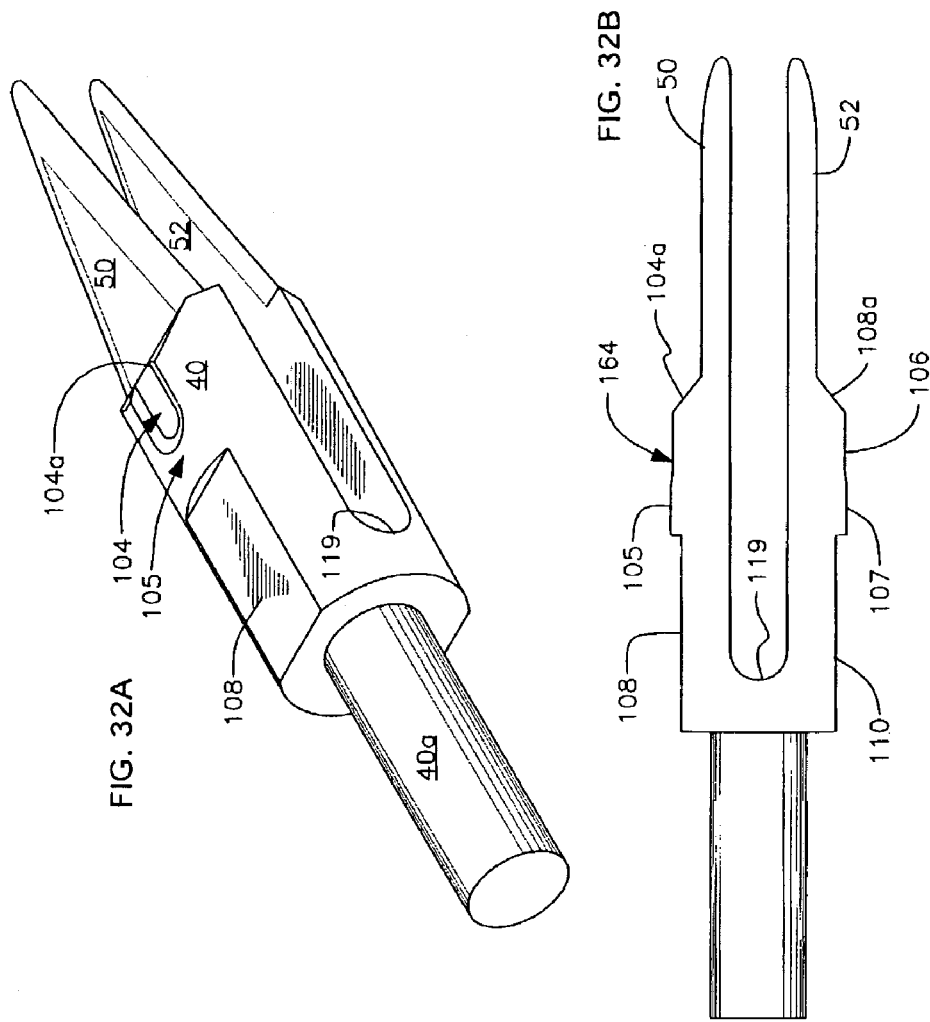
FIG. 32A is a perspective view of the clip of the sixth embodiment.
FIG. 32B is a side elevational view of said sixth embodiment clip.

As best depicted in FIGS. 32A and 32B, a first pair of recesses 104, 106 are formed in a leading end of a main body of clip 40 of this embodiment in diametrically opposed relation to one another. Both recesses have a leading edge in open communication with beveled surfaces 104a, 106a, respectively. A second pair of recesses 108, 110 are formed in the trailing end of the main body of clip 40 of this embodiment in diametrically opposed relation to one another. A pair of diametrically opposed raised areas 105, 107 (FIG. 32B) are thus provided between the recesses.

Figure 33:
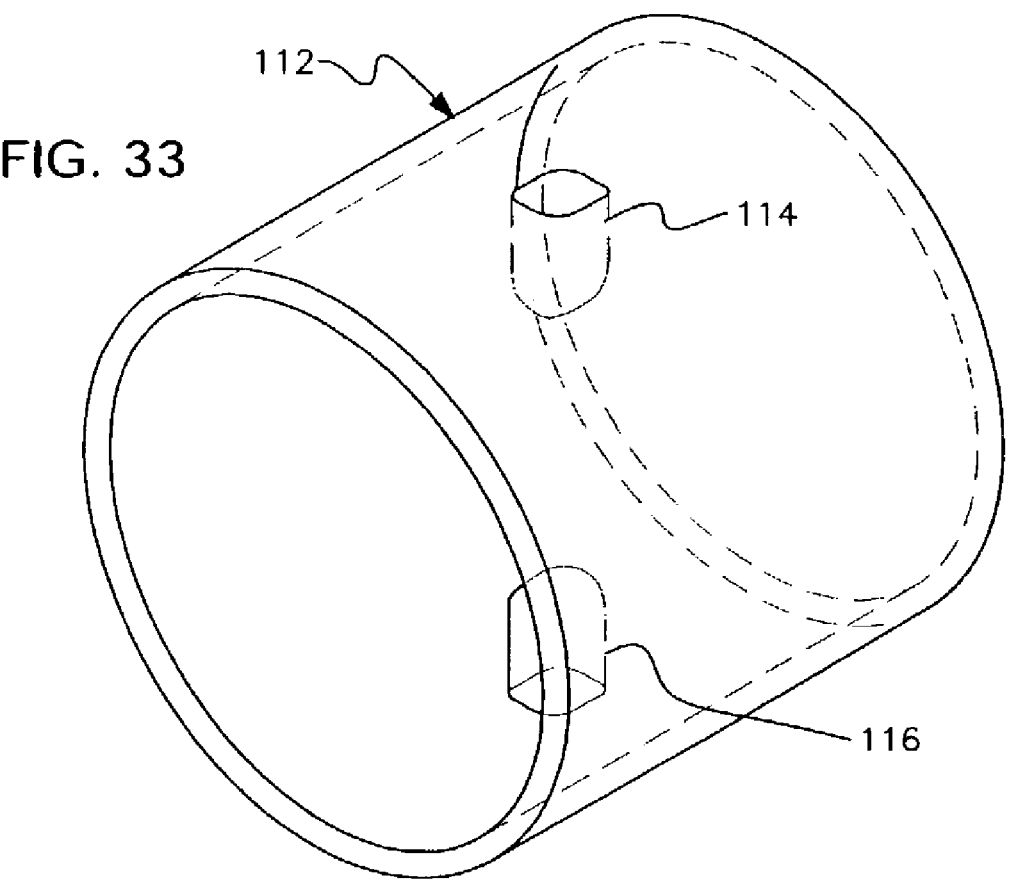
FIG. 33 is a perspective view of the locking cylinder of the sixth embodiment.
Figure 34:
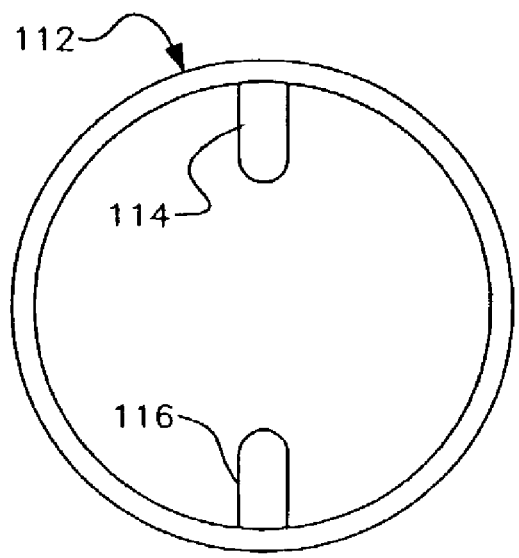
FIG. 34 is an end elevational view of the FIG. 33 locking cylinder.
Figure 35:
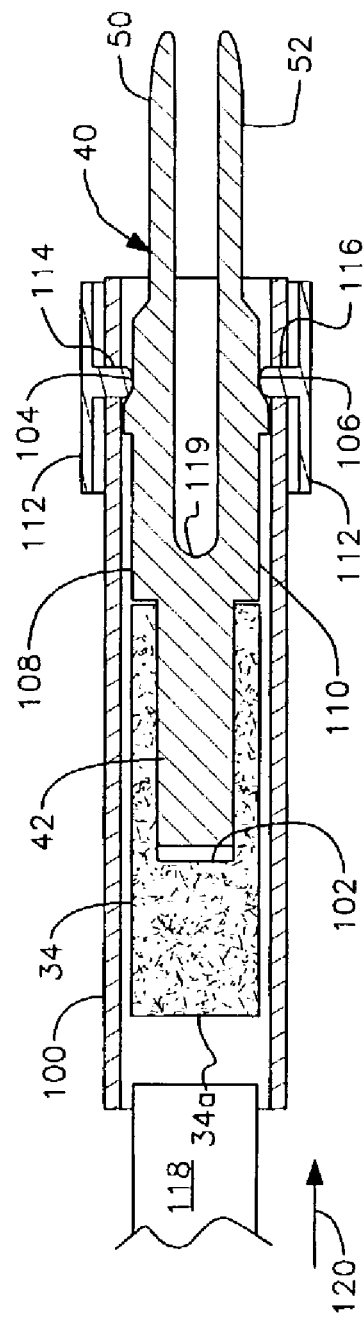
FIG. 35 is a longitudinal sectional view taken along line 35—35 in FIG. 31.

Cylindrical sleeve 112, depicted in perspective view in FIGS. 30, 33 and in end view in FIG. 34, has a pair of diametrically opposed, radially inwardly extending pins 114, 116 formed therein. As depicted in FIG. 30, a first opening 114a is formed in delivery catheter 100 to accommodate pin 114 and a second opening 116, diametrically opposed to opening 114a, is formed in delivery catheter 100 to accommodate pin 116.

Figure 31:
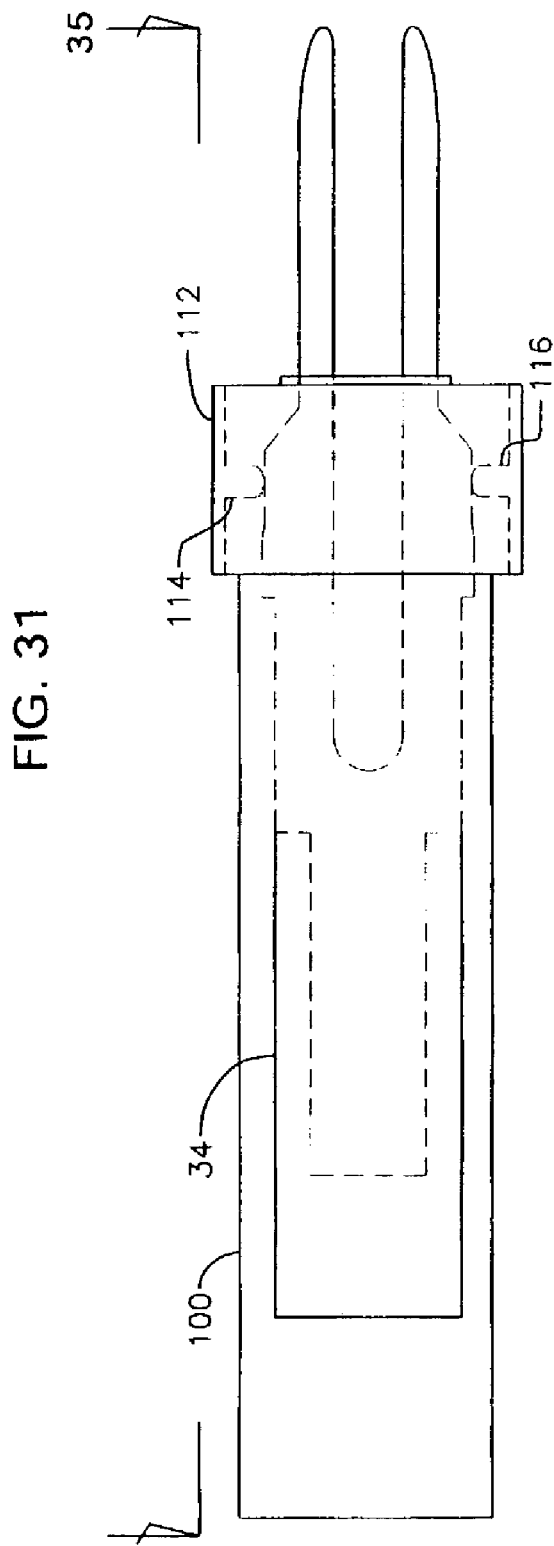
FIG. 31 is a side elevational view of the sixth embodiment.

When sleeve 112 is positioned in ensleeving relation to clip 40 as depicted in FIGS. 30 and 31, the leading end of delivery catheter 100 and the leading end of cylindrical sleeve 112 are in substantial alignment with one another and opposed jaws 50, 52 are in repose.

Figure 36:
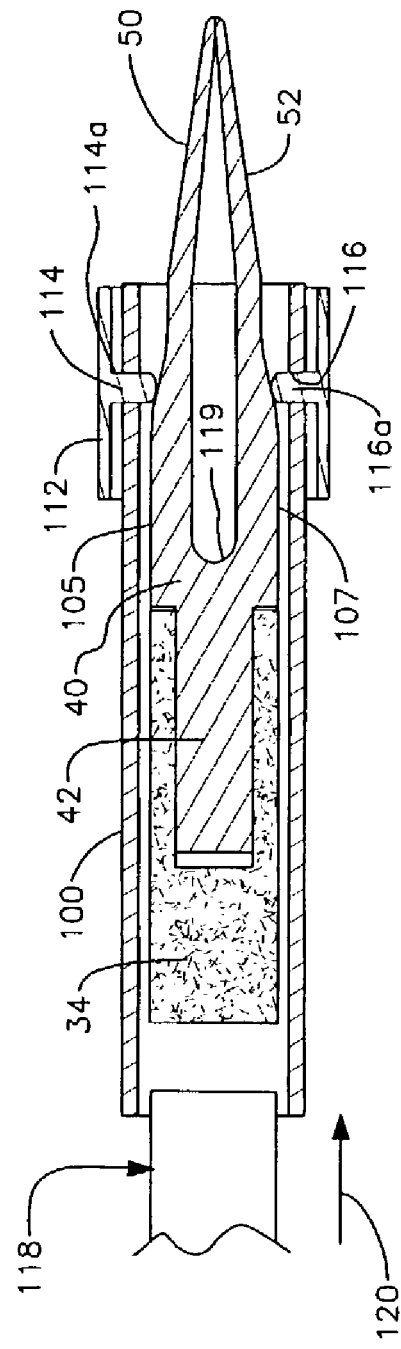
FIG. 36 is a longitudinal sectional view like that of FIG. 35 but when a plunger has driven the clip from its position of repose.

As depicted in FIG. 36, when plunger 118 is positioned in the lumen of delivery catheter 100 and is advanced in a trailing-to-leading direction as indicated by single-headed directional arrow 120, marker 34 drives clip 40 in the same direction and jaws 50, 52 are driven toward one another because pins 114, 116 are constrained against radial travel by cylindrical sleeve 112. Since pins 114, 116 cannot be displaced in a radially outward direction when they are compelled to slide out of recesses 104, 106, onto the raised surfaces formed in the main body, jaws 50, 52 must converge toward one another. The pivot point about which said jaws converge is denoted 119. Accordingly, the respective distal free ends of said jaws firmly grasp tissue therebetween, permanently anchoring clip 40 to said tissue. As in the earlier embodiments, this ensures that clip will remain attached to the tissue long after marker 34 has been bioabsorbed. Moreover, clip 40 will not migrate over time.

Further displacement of plunger 118 in the same direction causes pins 114, 116 to enter into registration with trailing recesses 108, 110, thereby releasing the pins and enabling withdrawal of delivery catheter 100 and cylindrical sleeve 112. The opposed jaws of the clip are not resilient so they remain in their closed configuration when the pressure on said pins is released.

As mentioned above, this invention is not limited to core biopsy needles that employ a vacuum. It has utility not only with coaxial needles, which do not employ a vacuum, but also with core biopsy needles where no vacuum is employed.

When a vacuum is applied to a core biopsy needle of the vacuum type, there is a possibility of taking in loose tissue not in the vicinity of the biopsy tract. Taking in such unwanted loose tissue may cause the marker to slide away from the biopsy site with the loose tissue. For example, where a breast is under compression, the marker may slide away when the breast compression is removed at the end of the procedure. Therefore, it is important to be able to attach the tissue marker directly into the biopsy site tract in the absence of a vacuum.

Figure 37:
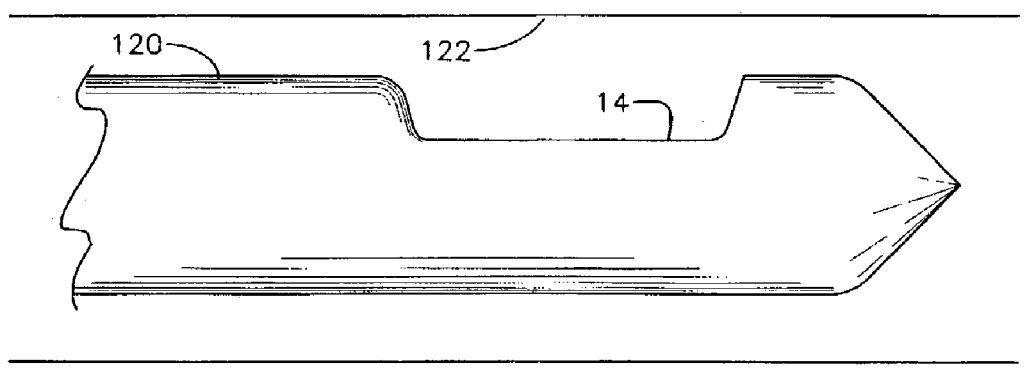
FIG. 37 is a side elevational view of a core biopsy needle of the type that does not employ a vacuum.
Figure 38:
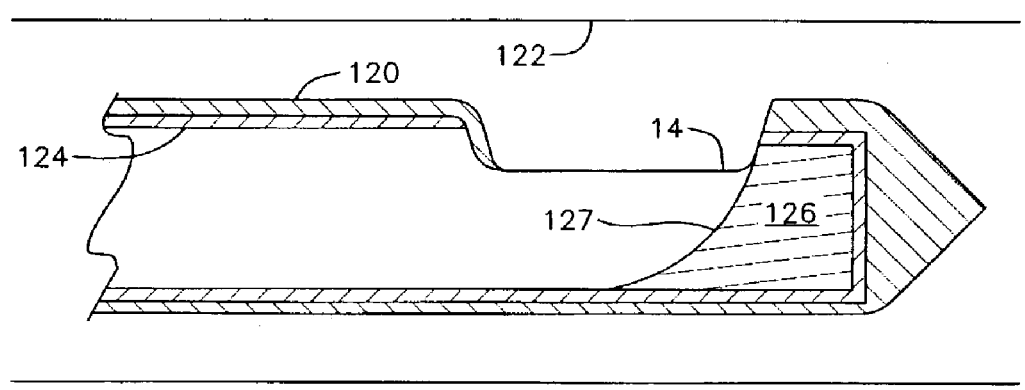
FIG. 38 is a longitudinal sectional view of a delivery catheter equipped with a ramp member, said delivery catheter being disposed within the lumen of the core biopsy needle of FIG. 37.

A seventh embodiment of the invention is depicted in FIG. 37. A core biopsy needle 120 of the type that does not employ a vacuum is positioned within a biopsy tract having biopsy tract wall 122. The invention is not limited to this particular example, it being understood that the tract could be formed by means other than a biopsy needle. FIG. 38 adds delivery catheter 124 having a ramp member 126 positioned at its distal end. Note that delivery catheter ramp 126 has an arcuate surface 127 formed therein on the proximal side thereof.

Figure 39:
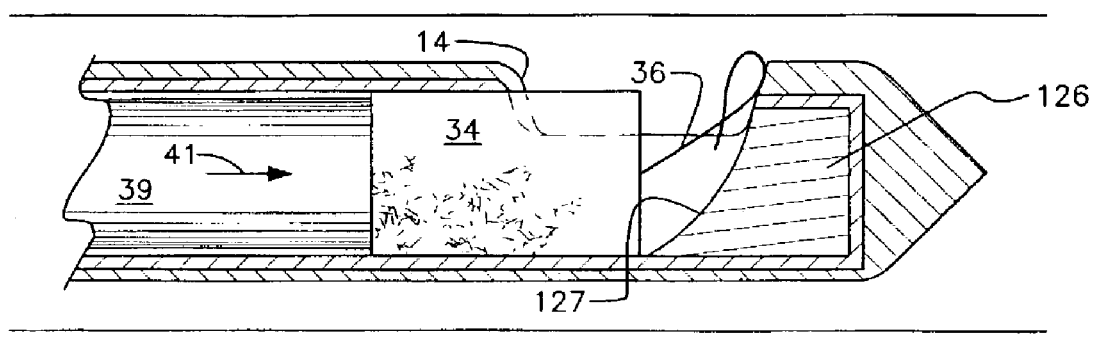
FIG. 39 is a longitudinal sectional view depicting a plunger advancing a marker in a lumen of said delivery catheter.

As depicted in FIG. 39, marker 34 having wire 36 or other suitable attachment means secured to a leading end thereof is pushed in a trailing-to-leading direction by plunger or pusher 39 in the direction indicated by single-headed directional arrow 41. Attachment means 36, which may be formed of metallic or non-metallic materials as long as such materials may be seen by at least one imaging technique, encounters arcuate surface 127 of ramp member 126 and is displaced toward port 14 formed in core biopsy needle 120.

Figure 40:
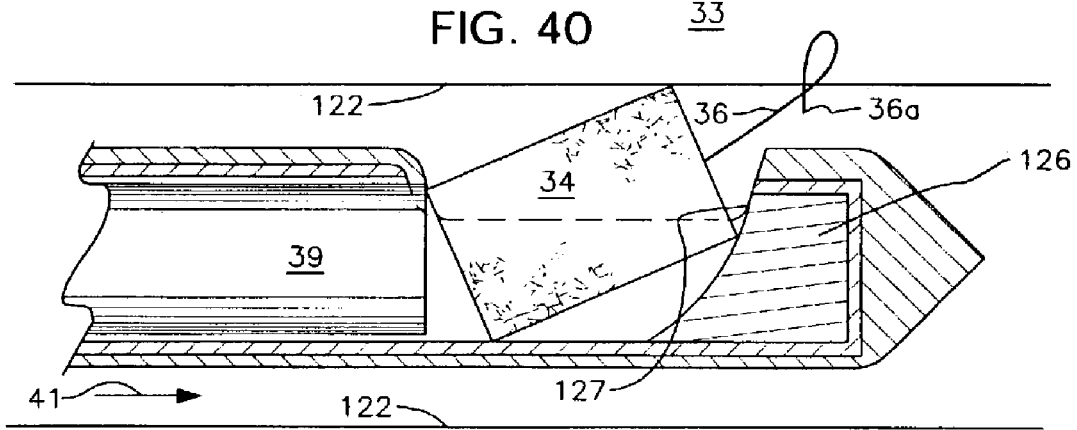
FIG. 40 is a view like that of FIG. 39, showing deployment of the attachment means and the marker secured thereto upon further advance of said plunger.

As indicated in FIG. 40, further advancement of pusher 39 drives attachment means 36 out of biopsy tract 122 and into tissue 33. In the example of FIGS. 39 and 40, attachment means 36 ends in a loop as illustrated. Note that a free end of loop 36, denoted 36a, engages tissue 33 in an anchoring manner so that neither attachment means 36 nor marker 34 will migrate from the point where said attachment means 36 enters into tissue 33.

Figure 41A:
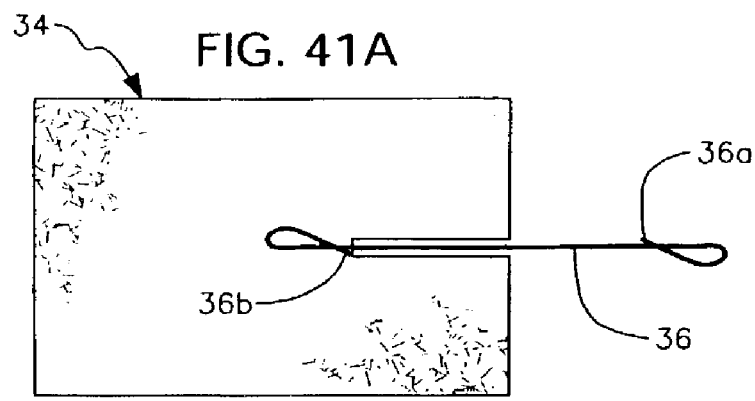
FIG. 41A is a side elevational view depicting a marker and a particular type of attachment means.

There are numerous ways for attaching marker 34 and attachment means 36 to one another. In FIG. 41A, a loop is formed in both ends of clip 36. Exposed leading end 36a engages tissue when marker 34 is deployed and embedded trailing end 36b engages the material from which marker 34 is formed, thereby preventing clip 36 from pulling ou of said marker 34.

Figure 41B:
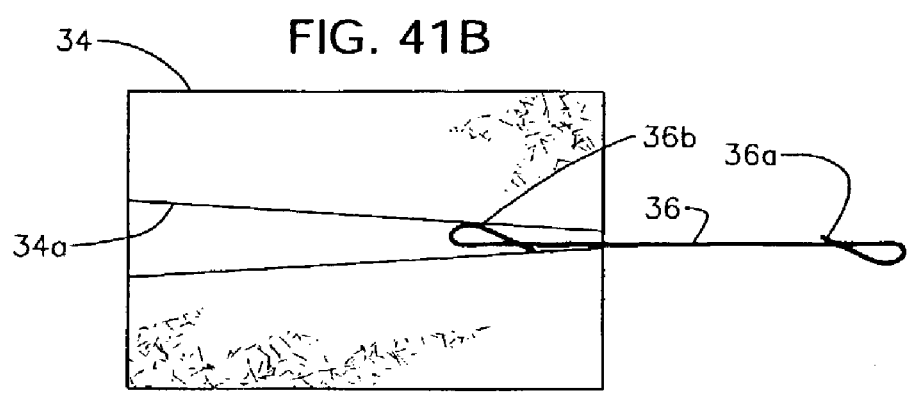
FIG. 41B is a side elevational view depicting a marker and a particular type of attachment means.
Figure 41C:
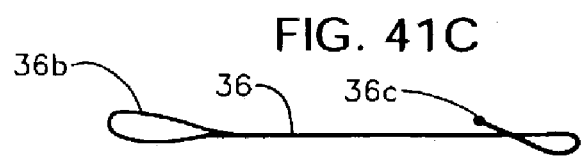
FIG. 41C is a side elevational view depicting a particular type of attachment means.
Figure 41D:
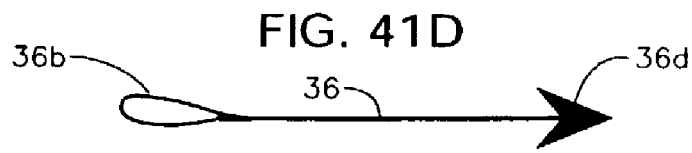
FIG. 41D is a side elevational view depicting a particular type of attachment means.

In FIG. 41B, bore 34a is formed in marker 34. The diameter of bore 34a tapers downwardly in a trailing-to-leading direction so that loop 36b formed in the trailing end of clip 36 is retained within said bore. In FIG. 41C, free end 36a of clip 36 is brazed as at 36c to cover the sharp cutting edge of said free end 36a. In FIG. 41D, said free end of clip 36 is formed into an arrowhead 36d. The trailing edges of the arrowhead serve as barbs that engage tissue.

Figure 42A:
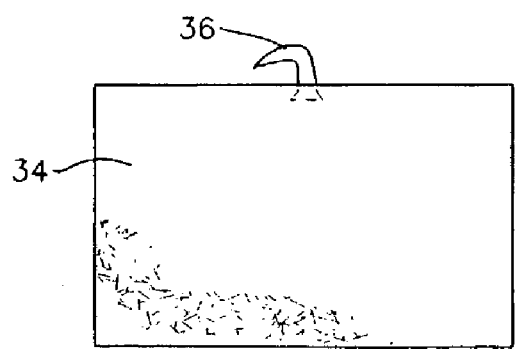
FIG. 42A depicts a marker having a particular type of attachment means when in its folded, undeployed configuration.
Figure 42B:
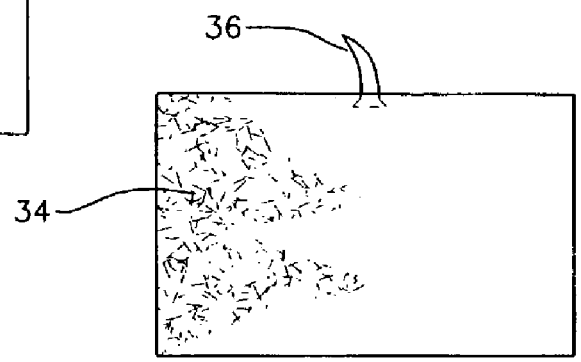
FIG. 42B depicts a marker having a particular type of attachment means when in its unfolded, deployed configuration.

Attachment means or clip 36 need not extend from the leading end of marker 34 is in the above-described embodiments. It may also extend from a midpoint of marker 34 as depicted in FIGS. 42A and 42B. In FIG. 42A, clip 36 is bent into a closed position. It may be held in such closed position by the interior sidewalls of a coaxial biopsy needle. Clip 36 may be formed of a resilient material such as nitinol so that when a pusher pushes it from the lumen of the coaxial biopsy needle, clip 36 returns to its original unbent shape as depicted in FIG. 42B. Its free end is then able to engage tissue and prevent migration of marker 34.

Figure 43A:
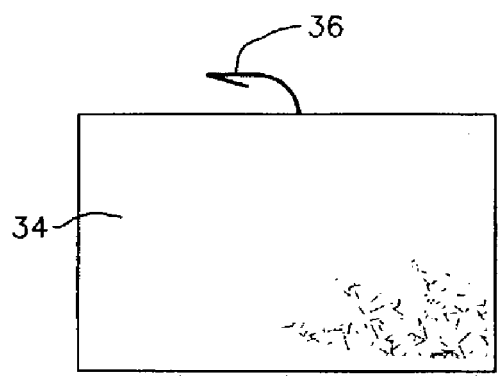
FIG. 43A depicts a marker having a particular type of attachment means when in its folded, undeployed configuration.
Figure 43B:
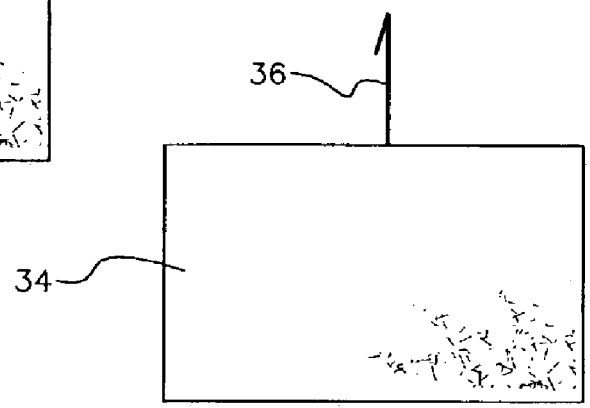
FIG. 43B depicts a marker having a particular type of attachment means when in its unfolded, deployed configuration.

A similar flexible and resilient clip 36 is attached to marker 34 mid-length thereof in the embodiment of FIGS. 43A and 43B. Clip 36 in this embodiment includes a barb at its distal free end for engaging tissue.

Figure 44A:
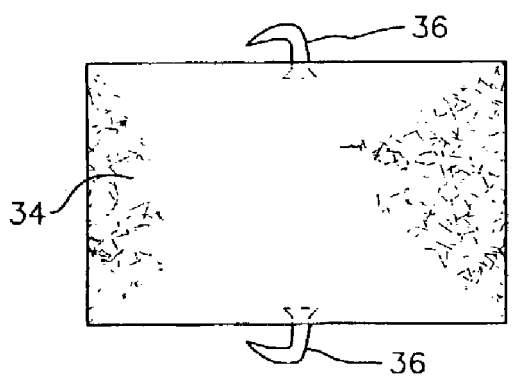
FIG. 44A depicts a marker having a particular type of attachment means when in its folded, undeployed configuration.
Figure 44B:
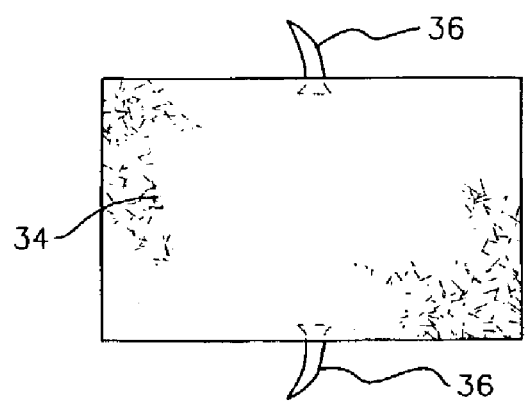
FIG. 44B depicts a marker having a particular type of attachment means when in its unfolded, deployed configuration.

As depicted in FIGS. 44A and 44B, there may be two or more flexible and resilient clips attached to marker 34, mid-length thereof. FIG. 44A depicts a pair of diametrically opposed clips 36, 36 when in their folded position, held down by the interior sidewalls of a coaxial biopsy needle, and FIG. 44B depicts said attachment means after their exit from said biopsy needle. There could be more than two of said clips 36 secured to marker 34. The depicted mid-length positioning thereof is not critical.

Figure 45A:
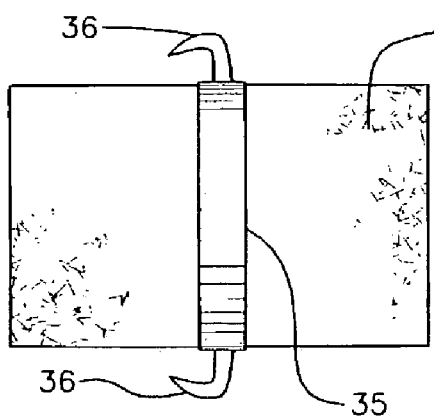
FIG. 45A depicts a marker having a particular type of attachment means when in its folded, undeployed configuration.
Figure 45B:
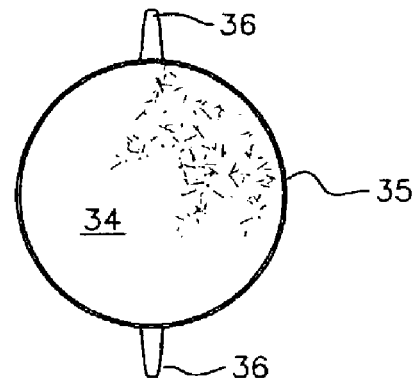
FIG. 45B is an end view of the marker and attachment means depicted in FIG. 45A.
Figure 45C:
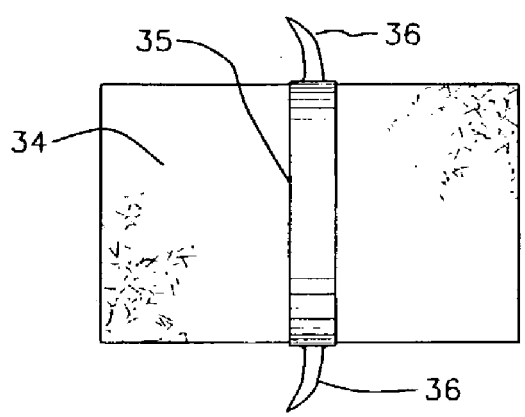
FIG. 45C depicts a marker having a particular type of attachment means when in its unfolded, deployed configuration.
Figure 45D:
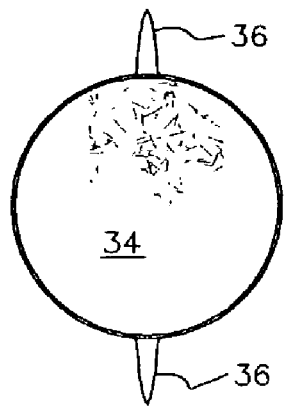
FIG. 45D is an end view of the marker and attachment means depicted in FIG. 45C.

Instead of embedding one end of clip 36 within marker 34, a pair of flexible and resilient clips 36 could be secured to a ring 35 that tightly encircles marker 34. Clips 36 are depicted in their folded down, undeployed configuration in the side view of FIG. 45A and in the end view of FIG. 45B and in their deployed, tissue-engaging configuration in the side view of FIG. 45C and in the end view of FIG. 45D.

Figure 46:
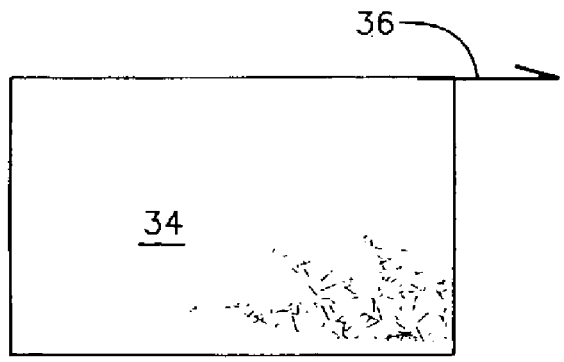
FIG. 46 is a side elevational view of a marker having a particular type of attachment means.

Yet another alternative embodiment is depicted in FIG. 46. Clip 36 is eccentrically mounted as depicted to the leading end of marker 34, near a peripheral edge of said marker 34. A barb is formed in the distal free end of clip 36 as illustrated. By placing the barbed clip away from the center of the leading end of marker 34, it is believed that clip 36 may better engage tissue. Also, the use of a minimal amount of metal or other suitable material for clip 36 is desirable in some applications.

Figure 47:
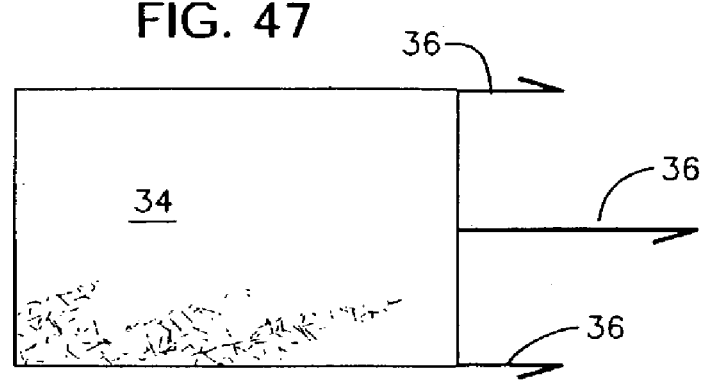
FIG. 47 is a side elevational view of a marker having a particular type of attachment means.

FIG. 47 depicts an embodiment having two barbed clips 36 at the leading end of marker 34, in diametrically opposed relation to one another, where said barbed clips are attached to said marker 34 near its outermost periphery as in the embodiment of FIG. 46. The central barbed clip of the first embodiment is also provided as still another attachment means. Note that, in this embodiment, central barbed clip 36 has a greater longitudinal extent than the peripherally mounted barbed clips 36, 36.

Figure 48:
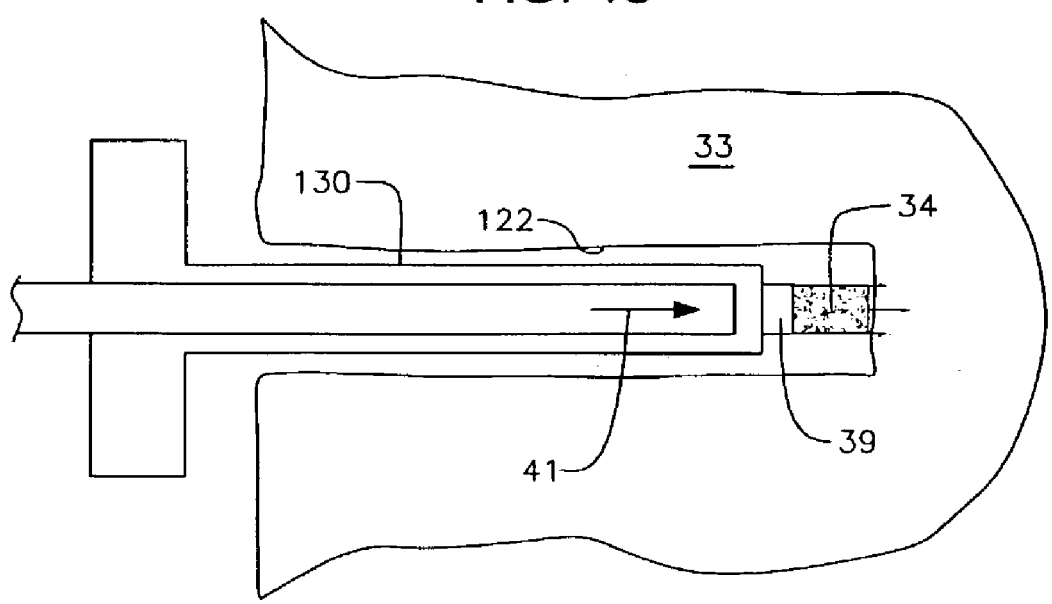
FIG. 48 is a side elevational view of a coaxial biopsy needle having a plunger for pushing a marker from a lumen of said coaxial biopsy needle so that an attachment means secured to said marker engages tissue external to said coaxial biopsy needle and anchors said marker against migration.

FIG. 48 depicts marker 34 of FIG. 47 being pushed into tissue 33 from a coaxial biopsy needle 130 by a plunger 39 that is pushed in a leading-to-trailing direction as indicated by arrow 41. Any marker of this invention may be pushed from the lumen of a coaxial needle by a plunger, not just the marker of said FIG. 47. A coaxial needle has particular utility when the marker has flexible and resilient attachment means that deploy upon exiting the lumen of a coaxial needle.

Although numerous embodiments have been depicted and described, many more examples could be given because many more embodiments become obvious in view of the disclosures made herein. All of such additional embodiments that flow naturally from the embodiments shown and described herein are within the scope of this invention.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An apparatus for marking a biopsy site, comprising:
   a biopsy needle having a lumen and a side port;
   a marker having a trailing end and a leading end;
   a straight configuration attachment means for engaging tissue having a trailing end embedded within said leading end of said marker and said straight configuration attachment means having a leading end disposed in leading relation to said leading end of said marker;
   a delivery catheter having a lumen and an anvil means fixedly secured within said lumen at a leading end of said delivery catheter;
   said anvil having a cavity with a concave bottom formed therein that causes bending of said straight configuration attachment means into a hook shape when said straight configuration attachment means is driven into said cavity;
   a side port formed in said delivery catheter, said anvil being disposed in leading relation to said side port;
   said delivery catheter disposed in said lumen of said biopsy needle and said side port of said delivery catheter being aligned with said side port of said biopsy needle;
   means for introducing a vacuum into said lumen of said delivery catheter, where said vacuum pulls tissue into said lumen of said delivery catheter when said means for introducing a vacuum is activated;
   said vacuum pulls tissue into said lumen by impaling said leading end of said straight configuration attachment means when said marker is displaced from a trailing end of said delivery catheter to a leading end of said delivery catheter;
   said leading end of said straight configuration attachment means encountering said concave bottom of said cavity and being bent into a hook after impaling said tissue disposed in said lumen of said delivery catheter;
   said marker and said straight configuration attachment means exiting said lumen of said delivery catheter through said aligned side ports when said vacuum is de-activated;
   whereby said marker and said straight configuration attachment means are secured to said tissue by said hook when said delivery catheter and biopsy needle are removed.

2. The apparatus of claim 1, wherein said straight configuration attachment means is a metal wire.

3. The apparatus of claim 1, wherein said straight configuration attachment means is formed of biologically absorbable materials.

4. The tissue marker means of claim 1, wherein said marker is formed of biologically absorbable materials.

5. A method for positioning a tissue marker at a tissue site, comprising the steps of:
   fixedly securing a trailing end of a straight attachment means for engaging a tissue into a leading end of a tissue marker;
   providing a delivery catheter having a side port and means for communicating a vacuum to a lumen of said delivery catheter;
   fixedly securing an anvil within said lumen of said delivery catheter at a leading end of said delivery catheter, in leading relation to said side port;
   forming a blind bore having a concave bottom in said anvil;
   introducing said tissue marker into said lumen of said delivery catheter from a trailing end of said delivery catheter;
   introducing said delivery catheter into a biopsy needle having a side port to pull said the respective side ports of the delivery catheter and biopsy needle are in substantial registration with one another;
   applying a vacuum to said biopsy needle so that tissue into the lumen of said delivery catheter;
   pushing said tissue marker toward said leading end of said delivery catheter so, that said straight attachment means pulls said tissue that has been pulled under vacuum into the lumen of said delivery catheter and then enters into said blind bore where a leading distal end of said straight attachment means is bent into a hook shape when said leading end encounters said concave bottom;
   removing said biopsy needle and delivery catheter from said tissue site so that only said marker and said straight attachment means remain at said site, said hook-shaped leading end of said straight attachment means engaging said tissue and preventing migration of said marker and of said straight attachment means.

6. An apparatus for anchoring a tissue marker to a tissue site, comprising:
   a tissue marker of generally cylindrical configuration;
   a first bore formed in said tissue marker in coincidence with a longitudinal axis of symmetry of said tissue marker, said first bore extending from a trailing end to a leading end of said tissue marker;
   an annular cavity formed in a leading end of said tissue marker in concentric relation to said bore;
   a clip having opposed jaws disposed in a normally closed configuration where respective free ends of said jaws are in close juxtaposition with one another;

said clip having a base formed in a trailing end of said clip, said base received within and fixedly secured to said annular cavity;

a second bore formed in said clip in coincidence with a longitudinal axis of symmetry of said clip, said second bore being in axial alignment with said first bore when said base of said clip is received within said annular cavity of said tissue marker;

a plunger having a first part of generally cylindrical configuration, said first part having a diameter substantially equal to a diameter of said tissue marker so that said first part and said tissue marker are adapted to be slideably received within a delivery catheter;

said plunger having a reduced diameter second part with a pointed leading end for penetrating tissue;

said second part having an elongate extent sufficient to extend sequentially through said first bore formed in said tissue marker, said second bore formed in said clip, and between said opposed jaws, said pointed leading end of said second part being disposed in leading relation to a leading end of said jaws when said plunger is fully introduced into said delivery catheter;

whereby said second part causes said opposed jaws to diverge from one another when inserted therebetween; and whereby said opposed jaws converge toward one another under said inherent bias when said second part of said plunger is withdrawn.

7. The apparatus of claim 6, wherein said clip is formed of a metallic material.

8. The apparatus of claim 6, wherein said clip is injection molded.

9. The apparatus of claim 6, wherein said clip is formed of biologically absorbable materials.

10. The apparatus of claim 6, wherein said marker is formed of biologically absorbable materials.

11. A method for anchoring a tissue marker to a tissue site, comprising:

providing a tissue marker of generally cylindrical configuration;

forming a first bore in said tissue marker in coincidence with a longitudinal axis of symmetry of said tissue marker so that said first bore extends from a trailing end to a leading end of said tissue marker;

forming an annular cavity in a leading end of said tissue marker in concentric relation to said bore;

providing a clip having opposed jaws disposed in a normally closed configuration where respective free ends of said jaws are in close juxtaposition with one another;

forming a base in a trailing end of said clip so that said base is received within and fixedly secured to said annular cavity;

forming a second bore in said clip in coincidence with a longitudinal axis of symmetry of said clip so that said second bore is in axial alignment with said first bore when said base of said clip is received within said annular cavity of said tissue marker, providing a plunger having a first part of generally cylindrical configuration, said first part having a diameter substantially equal to a diameter of said tissue marker so that said first part and said tissue marker are adapted to be slideably received within a delivery catheter;

providing said plunger with a reduced diameter second part with a pointed leading end for penetrating tissue;

forming said second part to have an elongate extent sufficient to extend sequentially through said first bore formed in said tissue marker, said second bore formed in said clip, and between said opposed jaws so that said pointed leading end of said second part is disposed in leading relation to a leading end of said jaws when said plunger is fully introduced into said delivery catheter;

said second part causing said opposed jaws to diverge from one another when inserted therebetween; and said opposed jaws converging toward one another under said inherent bias, thereby capturing tissue therebetween, when said second pan of said plunger is withdrawn.

12. An apparatus for anchoring a tissue marker to a tissue site, comprising:

a marker of generally cylindrical configuration having a leading end and a trailing end;

a first bore formed in said trailing end of said marker in coincidence with a longitudinal axis of symmetry of said marker;

a second bore formed in said leading end of said marker in coincidence with a longitudinal axis of symmetry of said marker;

said first and second bores being in open communication with one another and said second bore having a diameter greater than a diameter of said first bore;

a clip having a trailing end and a leading end, said trailing end adapted to be received within said second bore;

said clip having first and second opposed jaws disposed in normally open, parallel relation to one another;

a third bore formed in said trailing end of said clip in coincidence with a longitudinal axis of symmetry of said clip, said third bore being cross-shaped in transverse cross-section;

an inner plunger having a leading end having a circular transverse cross-section of predetermined extent and a pointed distal end of predetermined extent that is adapted to penetrate tissue, said pointed distal end being formed integrally with said leading end and being positioned in leading relation thereto;

said inner plunger having a trailing end having a circular transverse cross-section;

said inner plunger having a middle part having a cross-shaped transverse cross-section adapted to be slidingly received within said cross-shaped third bore, said middle part being formed integrally with said leading and trailing ends of said plunger and being disposed therebetween;

an outer plunger having a central bore adapted to slidingly receive said trailing end of said inner plunger;

said outer plunger having a leading end adapted to abuttingly engage said trailing end of said marker;

a first radially outwardly extending protuberance formed on a first jaw of said clip and a second radially outwardly extending protuberance formed on a second jaw of said clip;

said first protuberance having a first beveled trailing surface and said second protuberance having a second beveled trailing surface;

said first and second opposed jaws being driven toward one another when said marker is driven in a trailing to leading direction by said outer plunger, said leading end of said marker slideably engaging said first and second trailing beveled surfaces and driving said first and second trailing beveled surfaces toward one another;

said middle part of said inner plunger being positioned on a leading side of said third bore and said middle part being rotationally misaligned with said cross-shaped third bore so that a trailing end of said middle part is disposed in abutting relation to a leading end of said third bore, thereby preventing travel of said clip in a trailing-to-leading direction when said inner plunger is held against movement in said trailing-to-leading direction;

whereby said inner plunger is held against movement in said trailing-to-leading direction, thereby holding said clip against movement in said trailing-to-leading direction, and said outer plunger is displaced in a trailing-to-leading direction to drive said marker in said trailing-to-leading direction, said marker leading end entering into sliding engagement with said first and second trailing beveled surfaces, thereby driving said opposed jaws into converging relation with one another;

whereby respective leading ends of said opposed jaws are driven into engaging relation to one another by trailing-to-leading displacement of said outer plunger;

whereby when said jaws are fully embedded within said tissue, a part of said tissue is captured between said jaws;

whereby said marker is driven in a trailing-to-leading direction and slideably receives said trailing end of said clip into said second bore;

whereby longitudinal displacement of said inner plunger in said trailing-to-leading direction and rotation of said inner plunger about its longitudinal axis of symmetry until said middle part aligns with the cross-shaped cross section of said third bore, followed by retraction of said inner plunger in a leading-to-trailing direction until said inner plunger has exited said third bore leaves said clip secured to said tissue and said marker secured to said trailing end of said clip.

13. The apparatus of claim 12, further comprising a beveled surface formed in said leading end of said marker to facilitate sliding engagement of said first and second trailing beveled surfaces formed on said first and second jaws of said clip by said beveled surface formed in said leading end of said marker.

14. The apparatus of claim 12, wherein said clip is formed of a metallic material.

15. The apparatus of claim 12, wherein said clip is injection molded.

16. The apparatus of claim 12, wherein said clip is formed of biologically absorbable materials.

17. The apparatus of claim 12, wherein said marker is formed of biologically absorbable materials.

18. A method for anchoring a tissue marker to a tissue site, comprising the steps of:

forming a marker of generally cylindrical configuration so that it has a leading end and a trailing end;

forming a first bore in said trailing end of said marker in coincidence with a longitudinal axis of symmetry of said marker;

forming a second bore in said leading end of said marker in coincidence with a longitudinal axis of symmetry of said marker;

forming said first and second bores so that they are in open communication with one another and so that said second bore has a diameter greater than a diameter of said first bore;

providing a clip having a trailing end and a leading end, and adapting said trailing end so that it is received within said second bore formed in said leading end of said marker;

providing said clip with a pair of opposed jaws adapted to engage tissue therebetween;

forming a third bore in said trailing end of said clip in coincidence with a longitudinal axis of symmetry of said clip and forming said third bore so that it is cross-shaped in transverse cross-section;

providing an inner plunger having a leading end with a circular transverse cross-section of predetermined extent and a pointed distal end of predetermined extent that is adapted to penetrate tissue, said pointed distal end being formed integrally with said leading end and being positioned in leading relation thereto;

providing said inner plunger with a trailing end having a circular transverse cross-section;

providing said inner plunger with a middle part having a cross-shaped transverse cross-section that is adapted to be slidingly received within said cross-shaped third bore;

forming an outer plunger with a central bore adapted to slidingly receive said trailing end of said inner plunger;

providing said outer plunger with a leading end adapted to abuttingly engage said trailing end of said marker;

forming a first radially-outwardly extending protuberance on a first jaw of said clip and forming a second radially-outwardly extending protuberance on a second jaw of said clip;

forming a first beveled trailing surface on a trailing side of said first protuberance and forming a second beveled trailing surface on a trailing side of said second protuberance;

driving said first and second opposed jaws toward one another by driving said marker in a trailing-to-leading direction with said outer plunger so that said leading end of said marker slideably engages said first and second beveled trailing surfaces and drives said first and second beveled trailing surfaces toward one another;

said middle part of said inner plunger being positioned on a leading side of said third bore and said middle part being rotationally misaligned with said cross-shaped third bore so that a trailing end of said middle part is disposed in abutting relation to a leading end of said third bore;

whereby said inner plunger is held against movement in a longitudinal direction, thereby holding said clip against movement in said longitudinal direction, and said outer plunger is displaced in a trailing-to-leading direction to drive said marker and said clip in said trailing-to-leading direction, said marker leading end entering into sliding engagement with said first and second beveled surfaces, driving them into converging relation with one another;

whereby respective leading ends of said opposed jaws are driven into tissue by continued trailing-to-leading displacement of said outer plunger;

whereby when said jaws are fully embedded within said tissue, a part of said tissue is captured between said jaws;

whereby longitudinal displacement of said inner plunger in a trailing-to-leading direction and rotation of said inner plunger about its longitudinal axis of symmetry until said middle part aligns with the cross-shaped cross section of said third bore, followed by retraction of said inner plunger in a leading-to-trailing direction until said inner plunger has exited said third bore leaves said clip secured to said tissue and said marker secured to said trailing end of said clip.

19. The method of claim 18, further comprising the step of forming an annular bevel in said leading end of said marker to facilitate sliding engagement of said leading end of said marker and said first and second beveled trailing surfaces formed in said first and second protuberances, respectively.

20. An apparatus for anchoring a tissue marker to a tissue site, comprising:
a marker having an elongate cylindrical structure;
a cross-shaped bore formed in said marker by a first slot that intersects with a second slot, said first slot having a greater radial extent than said second slot;
a clip having opposed jaws that are disposed in parallel relation to one another when in a position of repose;
said clip having a base fixedly secured to said marker;
a cross-shaped bore formed in said base of said clip by a first slot that intersects with a second slot, said first slot having a greater radial extent than said second slot;
said bore formed in said marker and said bore formed in said base of said clip being in axial alignment with one another;
first and second laterally-outwardly projecting, external wings formed in said first and second jaws, respectively;
first and second laterally-inwardly projecting, internal wings formed in said first and second jaws, respectively;
a beveled trailing surface formed in each of said internal wings;
said first and second external wings being diametrically opposed to one another and said first and second internal wings being diametrically opposed to one another;
said first and second external wings having a swept back configuration to facilitate their entry into tissue;
a plunger having a pointed leading end and a cross-shaped transverse cross section that corresponds to the respective shapes of said slots formed in said marker;
said plunger being sequentially inserted into said bore formed in said marker and said bore formed in said trailing end of said clip so that said pointed distal end of said plunger is introduced into a space between said opposed jaws;
said plunger bearing against said beveled trailing surfaces formed in said internal wings and thereby causing said opposed jaws to diverge from one another;
whereby retracting said plunger so that it disengages from said slots formed in said clip, followed by rotating said plunger ninety degrees to align the cross-shaped transverse cross section of the plunger with said slots, and sequentially pulling said plunger out of said clip and marker enables said opposed jaws to close under an inherent bias, said jaws capturing tissue therebetween when so closed;
whereby said internal wings serve to engage said tissue and work in conjunction with said external wings to prevent retraction of said clip from said tissue; and
whereby said first and second external wings prevent reverse migration of said clip after said clip has penetrated said tissue.

21. The apparatus of claim 20, wherein said clip is formed of a metallic material.

22. The apparatus of claim 20, wherein said clip is injection molded.

23. The apparatus of claim 20, wherein said clip is formed of biologically absorbable materials.

24. The apparatus of claim 20, wherein said marker is formed of a biologically absorbable material.

25. A method for anchoring a tissue marker to a tissue site, comprising the steps of:
providing a marker having an elongate cylindrical structure;
forming a cross-shaped bore in said marker by forming a first slot that intersects with a second slot, said first slot having a greater radial extent than said second slot;
providing a clip having opposed jaws that are disposed in parallel relation to one another when in a position of repose;
fixedly securing a base of said clip to said marker;
forming a cross-shaped bore in said base of said clip by forming a first slot that intersects with a second slot, said first slot having a greater radial extent than said second slot;
positioning said bore formed in said marker and said bore formed in said base of said clip so that said bores are in axial alignment with one another;
forming first and second laterally-outwardly projecting external wings in said first and second jaws, respectively, and forming first and second laterally-inwardly projecting internal wings in said first and second jaws, respectively;
each of said internal wings having a bevel formed in a trailing surface thereof;
positioning said first and second external wings in diametrically opposed relation to one another and positioning said first and second internal wings in diametrically opposed relation to one another;
forming said first and second external wings so that they have a swept back configuration to facilitate their entry into tissue;
providing a plunger having a pointed leading end and a cross-shaped transverse cross section that corresponds to the respective shapes of said slots formed in said marker, said cross-shaped transverse cross-section forming protuberances that extend radially outwardly,
sequentially inserting said plunger into said bore formed in said marker and said bore formed in said trailing end of said clip so that said pointed distal end of said plunger is introduced into a space between said opposed jaws;
whereby said protuberances bear respectively against said trailing surfaces formed in said internal wings and thereby cause said opposed jaws to diverge from one another;
whereby retracting said plunger so that it disengages from said slots formed in said clip, followed by rotating said plunger ninety degrees to align the radially extending protuberances of said plunger with said slots, and sequentially pulling said plunger out of said clip and marker enables said opposed jaws to close under an inherent bias, said jaws capturing tissue therebetween when so closed;
whereby said trailing surfaces serve to engage said tissue and work in conjunction with said external wings to prevent retraction of said clip from said tissue; and
whereby said first and second external wings prevent reverse migration of said clip after said clip has penetrated said tissue.

26. An apparatus for anchoring a tissue marker to a tissue site, comprising:
- a clip having a main body, a base formed on a trailing end of said main body, and a pair of opposed jaws formed on a leading end of said main body;
- a marker having a blind cylindrical bore formed in a leading end thereof;
- said base being received within said blind cylindrical bore;
- said base being fixedly secured within said blind cylindrical bore;
- said pair of opposed jaws being disposed in substantially parallel relation to one another when in repose;
- a first pair of recesses formed in a leading end of said clip main body in diametrically opposed relation to one another;
- a second pair of recesses formed in a trailing end of said main body of said clip in diametrically opposed relation to one another;
- a pair of diametrically opposed raised areas formed in said main body between said leading and trailing ends;
- a pair of diametrically opposed recesses formed in said main body in interconnecting relation between respective trailing ends of said first pair of recesses and said respective raised parts;
- a delivery catheter adapted to ensleeve said marker and said clip;
- a cylindrical sleeve adapted to ensleeve said delivery catheter;
- a pair of diametrically opposed, radially inwardly extending pins formed in said cylindrical sleeve;
- a first opening formed in said delivery catheter to accommodate a first pin and a second opening formed in said delivery catheter in diametric opposition to said first opening to accommodate a second pin of said pair of pins;
- a leading end of said delivery catheter and a leading end of said cylindrical sleeve being in substantial alignment with one another and said opposed jaws being in repose when said cylindrical sleeve is positioned in ensleeving relation to said delivery catheter;
- positioning a plunger within a lumen of said delivery catheter in trailing relation to said marker;
- whereby advancing the plunger in a trailing-to-leading direction causes said marker to drive said clip in the same direction and causes said opposed jaws to be driven toward one another because said pins are constrained to slide up said beveled surfaces from said first and second recesses respectively onto said raised surfaces and said pins are constrained against radial outward travel by said cylindrical sleeve and because said pins cannot be displaced in a radially outward direction they drive said opposed jaws toward one another;
- whereby the respective distal free ends of said jaws firmly grasp tissue therebetween, permanently anchoring said clip to said tissue; and
- whereby continued pushing of said marker by said plunger drives said pins from said raised surfaces into said second pair of recesses, thereby releasing pressure from said pins and enabling withdrawal of said delivery catheter and cylindrical sleeve.

27. The apparatus of claim 26, wherein said clip is formed of a metallic material.

28. The apparatus of claim 26, wherein said clip is injection molded.

29. The apparatus of claim 26, wherein said clip is formed of biologically absorbable materials.

30. The apparatus of claim 26, wherein said marker is formed of biologically absorbable materials.

31. A method for anchoring a tissue marker to a tissue site, comprising the steps of:
- providing a clip having a main body, a base formed on a trailing end of said main body, and a pair of opposed jaws formed on a leading end of said main body;
- providing a marker having a blind cylindrical bore formed in a leading end thereof;
- positioning said base within said blind cylindrical bore;
- fixedly securing said base within said blind cylindrical bore;
- positioning said pair of opposed jaws in a position of repose where said jaws are in substantially parallel relation to one another;
- forming a first pair of recesses in a leading end of said clip main body in diametrically opposed relation to one another;
- forming a second pair of recesses in a trailing end of said main body of said clip in diametrically opposed relation to one another;
- forming a pair of diametrically opposed raised areas in said main body between said leading and trailing ends;
- forming a pair of diametrically opposed recesses in said main body in interconnecting relation between respective trailing ends of said first pair of recesses and said respective raised parts;
- providing a delivery catheter adapted to ensleeve said marker and said clip;
- providing a cylindrical sleeve adapted to ensleeve said delivery catheter;
- forming a pair of diametrically opposed, radially inwardly extending pins in said cylindrical sleeve;
- forming a first opening in said delivery catheter to accommodate a first pin and forming a second opening in said delivery catheter in diametric opposition to said first opening to accommodate a second pin of said pair of pins;
- positioning a leading end of said delivery catheter and a leading end of said cylindrical sleeve in substantial alignment with one another so that said opposed jaws are in repose when said cylindrical sleeve is positioned in ensleeving relation to said delivery catheter;
- positioning a plunger within a lumen of said delivery catheter in trailing relation to said marker;
- advancing the plunger in a trailing-to-leading direction to cause said marker to drive said clip in the same direction and to cause said opposed jaws to be driven toward one another because said pins are constrained to slide up said beveled surfaces from said first and second recesses respectively onto said raised surfaces and said pins are constrained against radial outward travel by said cylindrical sleeve and because said pins cannot be displaced in a radially outward direction they drive said opposed jaws toward one another;
- continuing to push said marker in said direction by said plunger to drive said pins from said raised surfaces into said second pair of recesses, thereby releasing pressure from said pins and enabling withdrawal of said delivery catheter and cylindrical sleeve;
- whereby respective distal free ends of said jaws firmly grasp tissue therebetween, permanently anchoring said clip to said tissue.

32. An apparatus for anchoring a tissue marker to a tissue site, comprising:
- a core biopsy needle having a side port near a leading end thereof;

a delivery catheter having a side port near a leading end thereof;

said delivery catheter being slideably disposed within a lumen of said core biopsy needle, said side port of said delivery catheter being in substantial juxtaposition with said side port of said core biopsy needle;

a ramp member disposed at a leading end of said delivery catheter, said ramp member including an arcuate curved surface formed in a trailing end thereof;

a marker disposed in a lumen of said delivery catheter, an attachment means having a trailing end secured to said marker and a leading end disposed in leading relation to said marker;

a barb means for engaging tissue formed in said leading end of said attachment means;

a plunger disposed in said lumen of said delivery catheter in trailing relation to said marker, said plunger adapted to push said marker into said ramp member so that said attachment means is pushed through said delivery catheter side port and said core biopsy needle side port so that said barb means formed in said leading end of said attachment means is embedded within tissue that surrounds said core biopsy needle;

whereby said marker is secured to said tissue and said barb maintains said marker against migration in the absence of a vacuum means for pulling tissue into said core biopsy needle or said delivery catheter.

33. The apparatus of claim 32, wherein said attachment means is formed of a metallic material.

34. The apparatus of claim 32, wherein said attachment means is injection molded.

35. The apparatus of claim 34, wherein said attachment means is formed of biologically absorbable materials.

36. The apparatus of claim 34, wherein said marker is formed of biologically absorbable materials.

37. A method for anchoring a tissue marker to a tissue site, comprising the steps of:

providing a core biopsy needle having a side port near a leading end thereof;

providing a delivery catheter having a side port near a leading end thereof;

slideably disposing said delivery catheter within a lumen of said core biopsy needle so that said side port of said delivery catheter is in substantial juxtaposition with said side port of said core biopsy needle;

positioning a ramp member at a leading end of said delivery catheter and forming in a trailing end of said ramp member an arcuate curved surface;

positioning a marker in a lumen of said delivery catheter;

securing a trailing end of an attachment means to a leading end of said marker so that a leading end of said attachment means is disposed in leading relation to said marker;

forming a barb means for engaging tissue in said leading end of said attachment means;

positioning a plunger in said lumen of said delivery catheter in trailing relation to said marker;

pushing said marker into said ramp member with said plunger so that said attachment means is pushed through said delivery catheter side port and said core biopsy needle side port and so that said barb means formed in said leading end of said attachment means is embedded within tissue that surrounds said core biopsy needle;

whereby said marker is secured to said tissue and said barb maintains said marker against migration in the absence of a vacuum means for pulling tissue into said core biopsy needle or said delivery catheter.

38. An apparatus adapted to identify a tissue site, comprising:

a delivery catheter having a lumen, said delivery catheter having a plunger disposed within said lumen, and said delivery catheter having a side port adjacent to a distal end of the delivery catheter which opens into said lumen;

a ramp disposed at said distal end of the delivery catheter, and said ramp extending from inside the lumen of said delivery catheter to said side port;

a tissue marker moveably disposed in said lumen of the delivery catheter in leading relation to said plunger;

said tissue marker having at least one tissue anchor secured thereto;

said plunger adapted to push said tissue marker through said lumen, up said ramp and through said side port.

39. The apparatus of claim 38, wherein said anchor is made of metal.

40. The apparatus of claim 38, wherein said anchor is a wire forming a loop and having an exposed end.

41. The apparatus of claim 38, wherein said expose end is sharp.

42. The apparatus of claim 38, wherein said exposed end is in the shape of an arrowhead.

43. The apparatus of claim 38, wherein said anchor includes a barb.

44. The apparatus of claim 38, wherein at least a portion of said tissue marker is bio-compatible.

45. The apparatus of claim 38, wherein said anchor is echogenic.

46. A method of identifying a tissue site comprising the steps of:

selecting a tissue marker which has an identifier portion and a barbed anchor secured to the identifier portion;

providing a catheter having a side port;

positioning the side port adjacent a tissue site to be marked;

urging said tissue marker out of said side port into attachment with the tissue site;

attaching the barbed anchor to the tissue site-by enabling the barbed anchor to reconfigure itself from a folded configuration to an unfolded configuration so that the barbed anchor is attached to the tissue.

* * * * *